(12) United States Patent
Veasey et al.

(10) Patent No.: US 9,610,409 B2
(45) Date of Patent: *Apr. 4, 2017

(54) DRIVE MECHANISMS SUITABLE FOR USE IN DRUG DELIVERY DEVICES

(71) Applicant: SANOFI-AVENTIS DEUTSCHLAND GMBH, Frankfurt am Main (DE)

(72) Inventors: Robert Frederick Veasey, Warwickshire (GB); Robert Perkins, Warwickshire (GB); David Aubrey Plumptre, Worcestershire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 177 days.

This patent is subject to a terminal disclaimer.

(21) Appl. No.: 14/319,381

(22) Filed: Jun. 30, 2014

(65) Prior Publication Data
US 2014/0316346 A1    Oct. 23, 2014

Related U.S. Application Data

(63) Continuation of application No. 12/941,702, filed on Nov. 8, 2010, now Pat. No. 9,028,454, which is a
(Continued)

(30) Foreign Application Priority Data

Mar. 3, 2003    (GB) .................................. 0304822.0

(51) Int. Cl.
*A61M 5/315*    (2006.01)
*A61M 5/24*    (2006.01)
(Continued)

(52) U.S. Cl.
CPC .......... *A61M 5/31551* (2013.01); *A61M 5/24* (2013.01); *A61M 5/3157* (2013.01);
(Continued)

(58) Field of Classification Search
CPC ................ A61M 5/24; A61M 5/31533; A61M 5/31535; A61M 5/31536; A61M 5/31541;
(Continued)

(56) References Cited

U.S. PATENT DOCUMENTS

| | | |
|---|---|---|
| 533,575 A | 2/1895 | Wilkens |
| 2,444,570 A | 7/1948 | Lawrence et al. |

(Continued)

FOREIGN PATENT DOCUMENTS

| | | |
|---|---|---|
| DE | 3609555 | 9/1987 |
| EP | 295075 | 12/1988 |

(Continued)

OTHER PUBLICATIONS

Reissue U.S. Appl. No. 10/442,855, "Injection Syringe", Filed May 21, 2003, including as-filed specification, drawings, abstract, and claims, as well as the reissue declaration and a list of documents found in image file wrapper.

(Continued)

*Primary Examiner* — Andrew Gilbert
(74) *Attorney, Agent, or Firm* — McDonnell Boehnen Hulbert & Berghoff LLP

(57) ABSTRACT

A drive mechanism suitable for use in drug delivery devices is disclosed. The drive mechanism may be used with injector-type drug delivery devices, such as those permitting a user to set the delivery dose. The drive mechanism may include a housing, a dose dial sleeve, and a drive sleeve. A clutch is configured to permit rotation of the drive sleeve and the dose dial sleeve with respect to the housing when the dose dial sleeve and drive sleeve are coupled through the clutch. Conversely, when the dose dial sleeve and drive sleeve are in a de-coupled state, rotation of the dose dial sleeve with respect to the housing is permitted and rotation of the drive sleeve with respect to the housing is prevented.

(Continued)

In the de-coupled state, axial movement of the drive sleeve transfers force in a longitudinal direction for actuation of a drug delivery device.

9 Claims, 13 Drawing Sheets

Related U.S. Application Data continuation of application No. 12/320,189, filed on Jan. 21, 2009, now Pat. No. 7,850,662, which is a continuation of application No. 11/520,598, filed on Sep. 14, 2006, now Pat. No. 7,935,088, which is a continuation of application No. 10/790,866, filed on Mar. 3, 2004, now abandoned.

(51) Int. Cl.
*A61M 5/32* (2006.01)
*A61M 5/31* (2006.01)

(52) U.S. Cl.
CPC .... *A61M 5/31528* (2013.01); *A61M 5/31533* (2013.01); *A61M 5/31535* (2013.01); *A61M 5/31536* (2013.01); *A61M 5/31541* (2013.01); *A61M 5/31546* (2013.01); *A61M 5/31563* (2013.01); *A61M 5/31568* (2013.01); *A61M 5/31585* (2013.01); *A61M 5/31593* (2013.01); *A61M 5/32* (2013.01); *A61M 5/3156* (2013.01); *A61M 5/31565* (2013.01); *A61M 5/31575* (2013.01); *A61M 5/31578* (2013.01); *A61M 2005/2407* (2013.01); *A61M 2005/3126* (2013.01); *A61M 2205/581* (2013.01); *A61M 2205/582* (2013.01)

(58) Field of Classification Search
CPC .......... A61M 5/31551; A61M 5/31565; A61M 5/31578
See application file for complete search history.

(56) References Cited

U.S. PATENT DOCUMENTS

| | | | |
|---|---|---|---|
| 2,717,597 A | 9/1955 | Hein, Jr. | |
| 2,722,931 A | 11/1955 | May | |
| 3,815,785 A | 6/1974 | Gilmont | |
| 4,470,317 A | 9/1984 | Sabloewski et al. | |
| 4,498,904 A | 2/1985 | Turner et al. | |
| 4,568,335 A | 2/1986 | Updike et al. | |
| 4,585,439 A | 4/1986 | Michel | |
| 4,592,745 A | 6/1986 | Rex et al. | |
| 4,833,379 A | 5/1989 | Kaibel et al. | |
| 4,863,072 A | 9/1989 | Perler | |
| 4,865,591 A | 9/1989 | Sams | |
| 4,883,472 A | 11/1989 | Michel | |
| 4,919,596 A | 4/1990 | Slate et al. | |
| 4,936,833 A | 6/1990 | Sams | |
| 4,973,318 A | 11/1990 | Holm | |
| 4,994,033 A | 2/1991 | Shockey et al. | |
| 5,017,190 A | 5/1991 | Simon et al. | |
| 5,030,209 A | 7/1991 | Wanderer et al. | |
| 5,112,317 A | 5/1992 | Michel | |
| 5,207,752 A | 5/1993 | Sorenson et al. | |
| 5,226,895 A | 7/1993 | Harris | |
| 5,246,417 A | 9/1993 | Haak et al. | |
| 5,257,987 A | 11/1993 | Athayde et al. | |
| 5,271,527 A | 12/1993 | Haber et al. | |
| 5,279,585 A | 1/1994 | Balkwill | |
| 5,279,586 A | 1/1994 | Balkwill | |
| 5,281,198 A | 1/1994 | Haber et al. | |
| 5,284,480 A | 2/1994 | Porter et al. | |
| 5,304,152 A | 4/1994 | Sams | |
| 5,308,340 A * | 5/1994 | Harris | A61J 1/1406 604/208 |
| 5,314,412 A | 5/1994 | Rex | |
| 5,318,540 A | 6/1994 | Athayde et al. | |
| 5,320,609 A | 6/1994 | Haber et al. | |
| 5,328,486 A | 7/1994 | Woodruff | |
| 5,331,954 A | 7/1994 | Rex et al. | |
| 5,370,629 A | 12/1994 | Michel et al. | |
| 5,380,297 A | 1/1995 | Wadman et al. | |
| 5,383,865 A | 1/1995 | Michel | |
| 5,440,976 A | 8/1995 | Giuliano et al. | |
| 5,445,606 A | 8/1995 | Haak et al. | |
| 5,447,150 A | 9/1995 | Bacon | |
| 5,478,316 A | 12/1995 | Bitdinger et al. | |
| 5,480,387 A | 1/1996 | Gabriel et al. | |
| 5,492,534 A | 2/1996 | Athayde et al. | |
| 5,505,704 A | 4/1996 | Pawelka et al. | |
| 5,545,147 A | 8/1996 | Harris | |
| 5,546,932 A | 8/1996 | Galli | |
| 5,547,131 A | 8/1996 | Brace | |
| 5,549,574 A | 8/1996 | Townsend | |
| 5,549,575 A | 8/1996 | Giambattista | |
| 5,582,598 A | 12/1996 | Chanoch | |
| 5,584,815 A | 12/1996 | Pawelka | |
| 5,591,136 A * | 1/1997 | Gabriel | A61M 5/31553 604/208 |
| 5,599,314 A | 2/1997 | Neill | |
| 5,611,783 A | 3/1997 | Mikkelsen | |
| 5,626,566 A | 5/1997 | Petersen et al. | |
| 5,645,052 A | 7/1997 | Kersey | |
| 5,674,204 A | 10/1997 | Chanoch | |
| 5,679,111 A | 10/1997 | Hjertman et al. | |
| 5,681,285 A | 10/1997 | Ford et al. | |
| 5,685,864 A | 11/1997 | Shanley et al. | |
| 5,688,251 A | 11/1997 | Chanoch | |
| 5,693,027 A | 12/1997 | Hansen et al. | |
| 5,709,662 A | 1/1998 | Olive et al. | |
| 5,716,990 A | 2/1998 | Bagshawe et al. | |
| 5,725,508 A | 3/1998 | Chanoch et al. | |
| 5,728,074 A | 3/1998 | Castellano et al. | |
| 5,728,075 A | 3/1998 | Levander | |
| 5,743,889 A | 4/1998 | Sams | |
| 5,755,692 A | 5/1998 | Manicom | |
| 5,823,998 A | 10/1998 | Yamagata | |
| 5,827,232 A | 10/1998 | Chanoch | |
| 5,843,036 A | 12/1998 | Olive et al. | |
| 5,882,718 A | 3/1999 | Pommer et al. | |
| 5,898,028 A | 4/1999 | Jensen et al. | |
| 5,921,966 A | 7/1999 | Bendek et al. | |
| 5,928,201 A | 7/1999 | Poulsen et al. | |
| 5,938,642 A | 8/1999 | Burroughs et al. | |
| 5,947,934 A | 9/1999 | Hansen et al. | |
| 5,951,530 A | 9/1999 | Steengaard et al. | |
| 5,954,689 A | 9/1999 | Poulsen | |
| 5,957,896 A * | 9/1999 | Bendek | A61M 5/24 222/309 |
| 5,961,495 A | 10/1999 | Walters et al. | |
| 5,961,496 A | 10/1999 | Nielsen et al. | |
| 5,980,491 A | 11/1999 | Hansen | |
| 5,984,900 A | 11/1999 | Mikkelsen | |
| 6,001,089 A * | 12/1999 | Burroughs | A61M 5/31551 604/208 |
| 6,003,736 A | 12/1999 | Ljunggren | |
| 6,004,297 A | 12/1999 | Steenfeldt-Jensen et al. | |
| 6,010,485 A | 1/2000 | Buch-Rasmussen et al. | |
| 6,033,376 A | 3/2000 | Rockley | |
| 6,033,377 A | 3/2000 | Rasmussen et al. | |
| 6,048,336 A | 4/2000 | Gabriel | |
| 6,059,755 A | 5/2000 | Michel | |
| 6,074,372 A | 6/2000 | Hansen | |
| 6,083,197 A | 7/2000 | Umbaugh | |
| 6,086,567 A | 7/2000 | Kirchhofer et al. | |
| 6,096,010 A | 8/2000 | Walters | |
| 6,110,149 A | 8/2000 | Klitgaard et al. | |
| 6,129,080 A | 10/2000 | Pitcher et al. | |
| 6,146,361 A | 11/2000 | DiBiasi et al. | |
| 6,193,698 B1 | 2/2001 | Kirchhofer et al. | |
| 6,221,046 B1 | 4/2001 | Burroughs et al. | |

(56) References Cited

U.S. PATENT DOCUMENTS

| | | | |
|---|---|---|---|
| 6,221,053 B1 * | 4/2001 | Walters | A61M 5/31551 604/208 |
| 6,231,540 B1 | 5/2001 | Smedegaard | |
| 6,235,004 B1 | 5/2001 | Steenfeldt-Jensen et al. | |
| 6,248,090 B1 | 6/2001 | Jensen et al. | |
| 6,248,095 B1 | 6/2001 | Giambattista et al. | |
| 6,258,062 B1 | 7/2001 | Thielen et al. | |
| 6,269,340 B1 | 7/2001 | Ford et al. | |
| 6,277,097 B1 | 8/2001 | Mikkelsen et al. | |
| 6,277,098 B1 | 8/2001 | Klitmose et al. | |
| 6,277,099 B1 | 8/2001 | Strowe et al. | |
| 6,277,101 B1 | 8/2001 | Kirchhofer et al. | |
| 6,281,225 B1 | 8/2001 | Hearst et al. | |
| 6,283,941 B1 | 9/2001 | Schoenfeld et al. | |
| 6,287,283 B1 | 9/2001 | Ljunggreen | |
| 6,302,869 B1 | 10/2001 | Klitgaard | |
| 6,312,413 B1 | 11/2001 | Jensen et al. | |
| 6,340,357 B1 | 1/2002 | Poulsen et al. | |
| 6,379,339 B1 | 4/2002 | Klitgaard et al. | |
| 6,383,167 B2 | 5/2002 | Kirchhofer et al. | |
| 6,514,230 B1 | 2/2003 | Munk et al. | |
| 6,547,763 B2 | 4/2003 | Steenfeldt-Jensen et al. | |
| 6,547,764 B2 | 4/2003 | Larsen et al. | |
| 6,562,011 B1 | 5/2003 | Buch-Rasmussen et al. | |
| 6,569,126 B1 | 5/2003 | Poulsen et al. | |
| 6,582,404 B1 * | 6/2003 | Klitgaard | A61M 5/31525 604/181 |
| 6,605,067 B1 | 8/2003 | Larsen | |
| 6,613,019 B2 | 9/2003 | Munk | |
| 6,663,602 B2 | 12/2003 | Moller | |
| 6,692,472 B2 | 2/2004 | Hansen et al. | |
| 6,716,198 B2 | 4/2004 | Larsen | |
| 6,726,661 B2 | 4/2004 | Munk et al. | |
| 6,770,288 B2 | 8/2004 | Duirs | |
| 6,796,970 B1 | 9/2004 | Klitmose et al. | |
| 6,893,415 B2 | 5/2005 | Madsen et al. | |
| 6,899,698 B2 | 5/2005 | Sams | |
| 6,899,699 B2 | 5/2005 | Enggaard | |
| 6,932,794 B2 | 8/2005 | Giambattista et al. | |
| 6,936,032 B1 | 8/2005 | Bush, Jr. et al. | |
| 6,945,961 B2 | 9/2005 | Miller et al. | |
| 7,008,399 B2 | 3/2006 | Larsen et al. | |
| 7,090,662 B2 | 8/2006 | Wimpenny et al. | |
| 7,094,221 B2 | 8/2006 | Veasey et al. | |
| 7,104,972 B2 | 9/2006 | Moller et al. | |
| 7,133,329 B2 | 11/2006 | Skyggebiera et al. | |
| 7,169,132 B2 | 1/2007 | Bendek et al. | |
| 7,175,055 B2 | 2/2007 | Hansen et al. | |
| 7,195,616 B2 | 3/2007 | Diller et al. | |
| 7,241,278 B2 | 7/2007 | Moller | |
| 7,291,132 B2 | 11/2007 | DeRuntz et al. | |
| 7,316,670 B2 | 1/2008 | Graf et al. | |
| 7,361,161 B2 | 4/2008 | Bainton | |
| 7,553,299 B2 | 6/2009 | Veasey et al. | |
| 7,736,343 B2 | 6/2010 | Marshall et al. | |
| 7,771,400 B2 * | 8/2010 | Nielsen | A61M 5/24 604/207 |
| 7,850,662 B2 * | 12/2010 | Veasey | A61M 5/31546 604/207 |
| 7,905,867 B2 | 3/2011 | Veasey et al. | |
| 7,918,833 B2 | 4/2011 | Veasey et al. | |
| 7,935,088 B2 * | 5/2011 | Veasey | A61M 5/31546 604/207 |
| 8,021,345 B2 | 9/2011 | Veasey et al. | |
| 8,512,297 B2 * | 8/2013 | Veasey | A61M 5/31546 604/209 |
| 8,608,709 B2 * | 12/2013 | Moller | A61M 5/24 604/110 |
| 8,679,069 B2 | 3/2014 | Veasey et al. | |
| 9,028,454 B2 * | 5/2015 | Veasey | A61M 5/31546 604/211 |
| 9,233,211 B2 * | 1/2016 | Veasey | A61M 5/31535 |
| 2001/0034507 A1 | 10/2001 | Kirchhofer et al. | |
| 2002/0007154 A1 | 1/2002 | Hansen et al. | |
| 2002/0052578 A1 | 5/2002 | Moller | |
| 2002/0077852 A1 | 6/2002 | Ford et al. | |
| 2002/0120235 A1 | 8/2002 | Enggaard | |
| 2002/0165499 A1 | 11/2002 | Slate et al. | |
| 2003/0039679 A1 | 2/2003 | Duirs | |
| 2003/0050609 A1 | 3/2003 | Sams | |
| 2003/0172924 A1 | 9/2003 | Staniforth et al. | |
| 2004/0059299 A1 | 3/2004 | Moller | |
| 2004/0127858 A1 | 7/2004 | Bendek et al. | |
| 2004/0186431 A1 | 9/2004 | Graf et al. | |
| 2004/0210199 A1 | 10/2004 | Atterbury et al. | |
| 2004/0236282 A1 | 11/2004 | Braithwaite | |
| 2004/0249348 A1 | 12/2004 | Wimpenny et al. | |
| 2004/0260247 A1 | 12/2004 | Veasey et al. | |
| 2004/0267207 A1 | 12/2004 | Veasey et al. | |
| 2004/0267208 A1 | 12/2004 | Veasey et al. | |
| 2005/0004529 A1 | 1/2005 | Veasey et al. | |
| 2005/0019400 A1 | 1/2005 | Deveney et al. | |
| 2005/0033244 A1 | 2/2005 | Veasey et al. | |
| 2005/0055011 A1 | 3/2005 | Enggaard | |
| 2005/0113765 A1 | 5/2005 | Veasey et al. | |
| 2005/0205083 A1 | 9/2005 | Staniforth et al. | |
| 2005/0209570 A1 | 9/2005 | Moller | |
| 2005/0268915 A1 | 12/2005 | Wassenaar et al. | |
| 2006/0206057 A1 | 9/2006 | DeRuntz et al. | |
| 2006/0264839 A1 | 11/2006 | Veasey et al. | |
| 2007/0093761 A1 | 4/2007 | Veasey | |
| 2007/0123829 A1 | 5/2007 | Atterbury et al. | |
| 2009/0275916 A1 | 11/2009 | Harms et al. | |
| 2010/0042054 A1 | 2/2010 | Elahi et al. | |
| 2012/0053528 A1 | 3/2012 | Bollenbach et al. | |

FOREIGN PATENT DOCUMENTS

| | | |
|---|---|---|
| EP | 327910 | 8/1989 |
| EP | 359070 B1 | 3/1990 |
| EP | 450905 | 10/1991 |
| EP | 498737 | 8/1992 |
| EP | 554996 | 8/1993 |
| EP | 594349 | 4/1994 |
| EP | 608343 B1 | 8/1994 |
| EP | 702970 | 3/1996 |
| EP | 0673482 | 4/1998 |
| EP | 879610 | 11/1998 |
| EP | 0937471 | 8/1999 |
| EP | 0937476 | 8/1999 |
| EP | 0937477 | 8/1999 |
| EP | 1250167 B1 | 7/2005 |
| EP | 1294418 | 7/2005 |
| EP | 1570876 A2 | 7/2005 |
| EP | 1855743 | 12/2008 |
| FR | 2583291 | 12/1986 |
| FR | 2767479 | 2/1999 |
| GB | 735443 | 8/1955 |
| GB | 1232899 | 5/1971 |
| GB | 2141799 | 1/1985 |
| JP | 05337179 | 12/1993 |
| JP | 06296691 | 10/1994 |
| RU | 2111019 | 5/1998 |
| WO | 8907463 | 8/1989 |
| WO | 9009202 | 8/1990 |
| WO | 9110460 | 7/1991 |
| WO | 9114467 | 10/1991 |
| WO | 9307922 | 4/1993 |
| WO | 9419034 | 9/1994 |
| WO | 9625965 | 8/1996 |
| WO | 9626754 | 9/1996 |
| WO | 9638190 | 12/1996 |
| WO | 9736626 | 10/1997 |
| WO | 9810813 | 3/1998 |
| WO | 9856436 | 12/1998 |
| WO | 9857688 | 12/1998 |
| WO | 9916487 | 4/1999 |
| WO | 99/38554 | 8/1999 |
| WO | 9938554 | 8/1999 |
| WO | 0110484 | 2/2001 |
| WO | 0119434 | 3/2001 |
| WO | 02053214 | 7/2002 |

(56) References Cited

FOREIGN PATENT DOCUMENTS

| WO | 02092153 | 11/2002 |
|---|---|---|
| WO | 03080160 | 10/2003 |
| WO | 2011051366 | 5/2011 |

OTHER PUBLICATIONS

Reissue U.S. Appl. No. 10/960,900, "Injection Syringe", Filed Oct. 7, 2004, including as-filed specification, drawings, abstract, and claims, as well as the reissue declaration and a list of documents found in image file wrapper.
Reissue U.S. Appl. No. 11/121,331, "Injection Syringe", Filed Dec. 18, 2006, including as-filed specification, drawings, abstract, and claims, as well as the reissue declaration and a list of documents found in image file wrapper.
Reissue U.S. Appl. No. 11/640,610, "Injection Syringe", Filed May 3, 2005, including as-filed specification, drawings, abstract, and claims, as well as the reissue declaration and a list of documents found in image file wrapper.
US Office Action mailed Mar. 14, 2006 in U.S. Appl. No. 10/790,866.
US Office Action mailed Dec. 18, 2008 in U.S. Appl. No. 10/960,600.
US Office Action mailed Apr. 17, 2009 in U.S. Appl. No. 11/121,331.
US Office Action mailed Apr. 17, 2009 in U.S. Appl. No. 11/640,610.

* cited by examiner

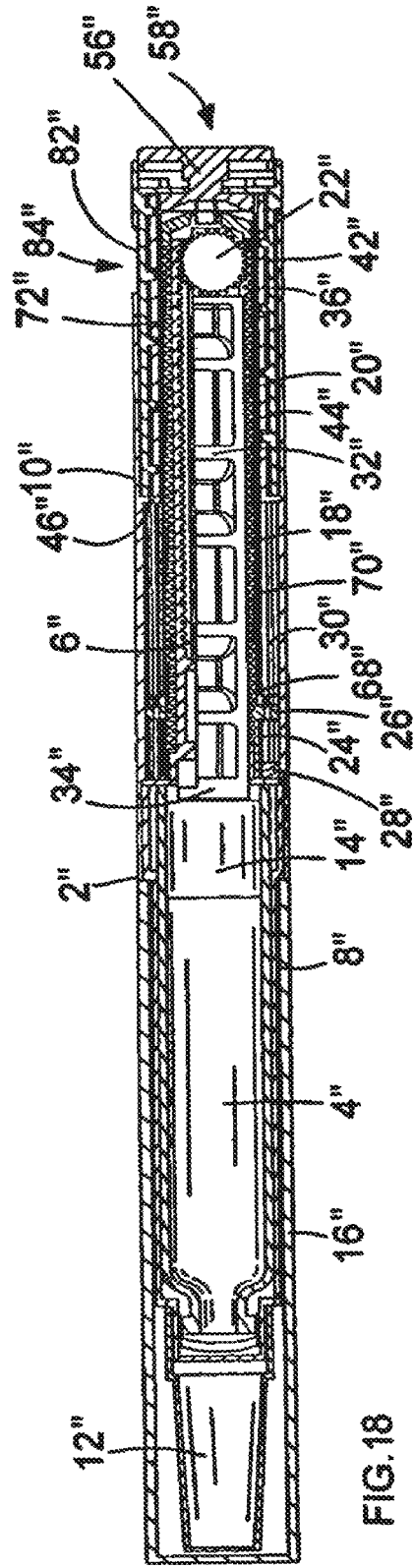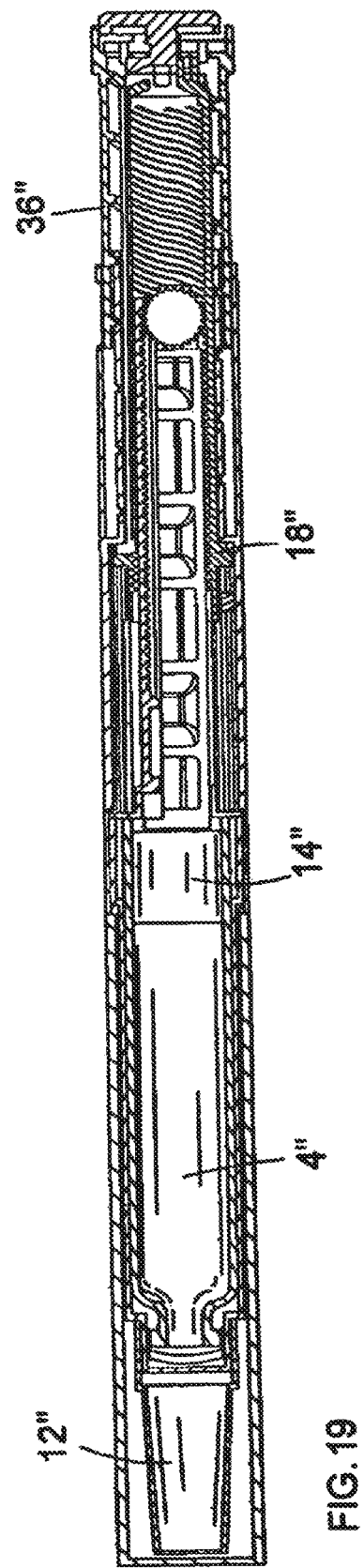
FIG. 18
FIG. 19

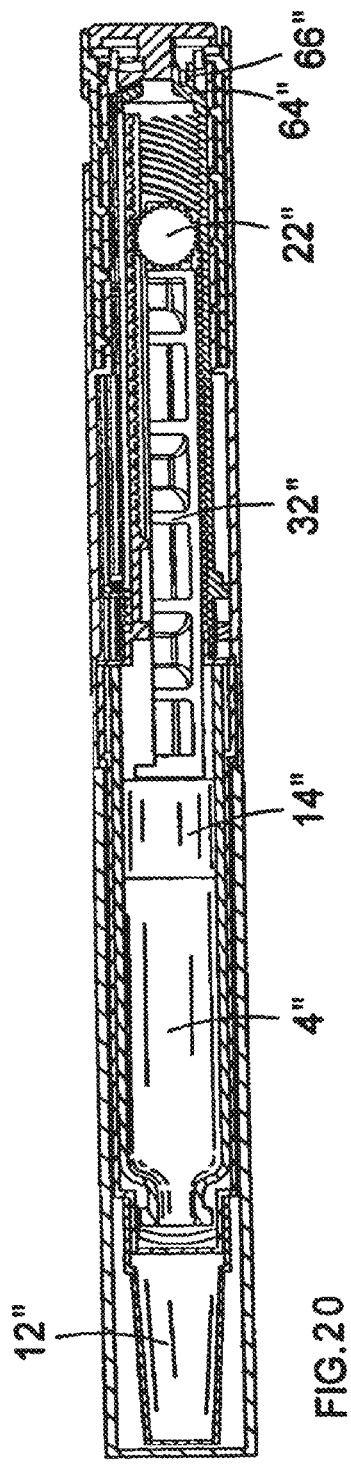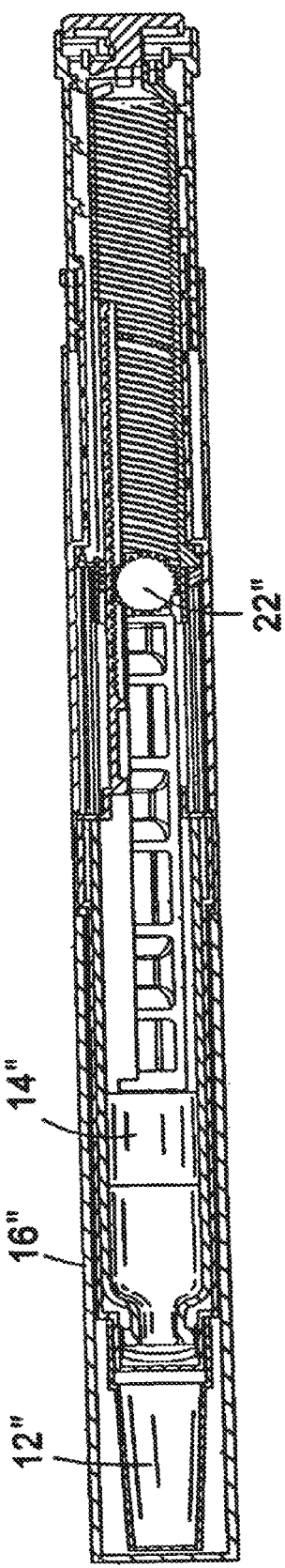

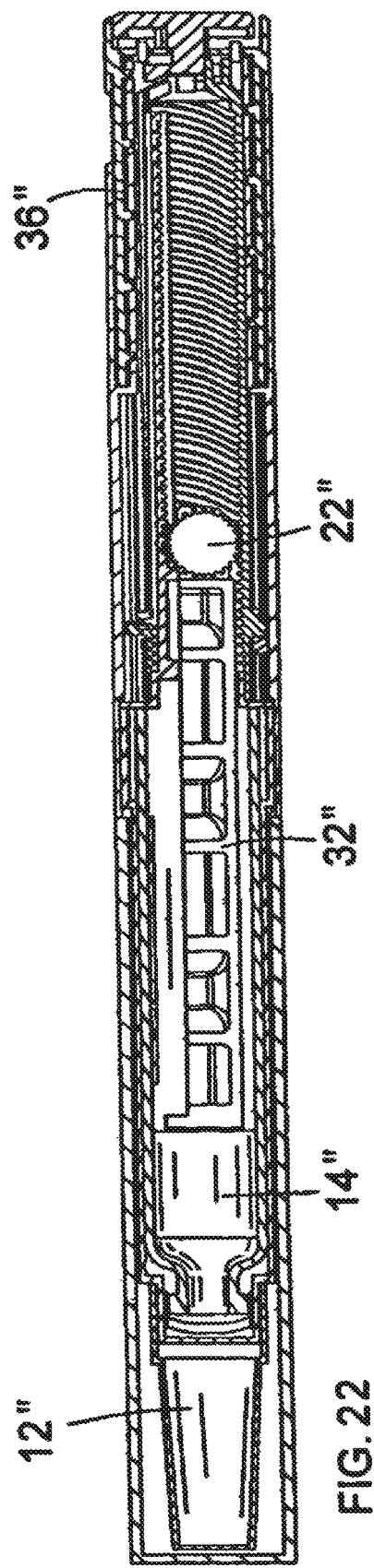

DRIVE MECHANISMS SUITABLE FOR USE IN DRUG DELIVERY DEVICES

CROSS REFERENCE TO RELATED APPLICATIONS

The present application is a continuation application of U.S. patent application Ser. No. 12/941,702, filed Nov. 8, 2010, now U.S. Pat. No. 9,028,454, which is a continuation application of U.S. patent application Ser. No. 12/320,189, filed Jan. 21, 2009, now U.S. Pat. No. 7,850,662, which is a continuation application of U.S. patent application Ser. No. 11/520,598, filed Sep. 14, 2006, now U.S. Pat. No. 7,935,088, which is a continuation application of U.S. patent application Ser. No. 10/790,866, filed Mar. 3, 2004, abandoned, and claims priority to GB Patent Application No. 0304822.0, filed Mar. 3, 2003, the entire contents of each of which are incorporated herein by reference.

TECHNICAL FIELD

The present invention relates to drive mechanisms suitable for use in drug delivery devices, in particular pen-type injectors, having dosage setting means, enabling the administration of medicinal products from a multi-dose cartridge. In particular, the present invention relates to such drug delivery devices where a user may set the dose.

BACKGROUND

Such drug delivery devices have application where regular injection by persons without formal medical training occurs, i.e., patients. This is increasingly common amongst those having diabetes where self-treatment enables such persons to conduct effective management of their diabetes.

These circumstances set a number of requirements for drug delivery devices of this kind. The device must be robust in construction, yet easy to use in terms of the manipulation of the parts, understanding by a user of its operation and the delivery of the required dose of medicament. Dose setting must be easy and unambiguous. In the case of those with diabetes, many users will be physically infirm and may also have impaired vision requiring the drive mechanism to have low dispensing force and an easy to read dose setting display. Where the device is to be disposable rather than reusable, the device should be cheap to manufacture and easy to dispose of (preferably being suitable for recycling). To meet these requirements the number of parts required to assemble the device and the number of material types the device is made from need to be kept to a minimum.

User operated drug delivery devices are well known within the medical field.

In U.S. Pat. No. 5,304,152 a dispensing device is disclosed which has a body length to plunger length ratio of about 1:1 in order to allow the dispensing of relatively large doses. Whilst this device provides many improvements over the prior art the easy correction of a set overdose remains unresolved without either dispensing the set amount of fluid or dismantling the cartridge.

WO 9938554 A2 teaches an injection syringe for apportioning set doses of a medicine from a cartridge wherein a drive mechanism comprising a unidirectional coupling (i.e., a ratchet) is disclosed which allows correction of a set overdose without dispensing the set amount of fluid or requiring the dismantling of the cartridge.

Surprisingly it was found that the drive mechanism according to instant invention without having a unidirectional coupling provides a valuable technical alternative for drive mechanisms, wherein reduced force is needed to actuate the mechanism. This is achieved by the introduction of a clutch means as defined by instant invention. The drive mechanism according to instant invention further provides the advantage of intuitive and easy to use correction of a set dose.

SUMMARY

According to a first aspect of the present invention, a drive mechanism for use in a drug delivery device is provided comprising:

a housing having a helical thread;

a dose dial sleeve having a helical thread engaged with the helical thread of the said housing;

a drive sleeve releasibly connected to the said dose dial sleeve;

and a clutch means located between the dose dial sleeve and the drive sleeve;

characterized in that, a) when the dose dial sleeve and the drive sleeve are coupled, the dose dial sleeve and the drive sleeve are allowed to rotate with respect to the housing; and b) when the dose dial sleeve and the drive sleeve are de-coupled, rotation of the dose dial sleeve with respect to the housing is allowed, whilst rotation of the drive sleeve with respect to the housing is not allowed, whereby axial movement of the drive sleeve is allowed so that a force is transferred in the longitudinal direction to the proximal end of the drug delivery device.

In a preferred embodiment of the drive mechanism of instant invention the said drive mechanism further comprises a piston rod adapted to operate through the housing and transfer the said force in the said longitudinal direction to the proximal end of the drug delivery device.

In another preferred embodiment of the drive mechanism of instant invention the said dose dial sleeve further comprises a helical thread, which has the same lead as the lead of the helical thread of the said drive sleeve.

In a more specific embodiment of instant invention, the drive mechanism further comprises a nut, which is rotatable with respect to the drive sleeve and axially displaceable but not rotatable with respect to the housing.

The term "drug delivery device" according to instant invention shall mean a single-dose or multi-dose, or re-useable device designed to dispense a selected dose of a medicinal product, preferably multiple selected doses, e.g. insulin, growth hormones, low molecular weight heparins, and their analogues and/or derivatives etc. Said device may be of any shape, e.g. compact or pen-type. Dose delivery may be provided through a mechanical (optionally manual) or electrical drive mechanism or stored energy drive mechanism, such as a spring, etc. Dose selection may be provided through a manual mechanism or electronic mechanism. Additionally, said device may contain components designed to monitor physiological properties such as blood glucose levels, etc. Furthermore, the said device may comprise a needle or may be needle-free. In particular, the term "drug delivery device" shall mean a disposable multi-dose pen-type device having mechanical and manual dose delivery and dose selection mechanisms, which is designed for regular use by persons without formal medical training such as patients. Preferably, the drug delivery device is of the injector-type.

The term "housing" according to instant invention shall preferably .mean any exterior housing ("main housing", "body", "shell") or interior housing ("insert", "•inner body") having a helical thread. The housing may be designed to enable the safe, correct, and comfortable handling of the drug delivery device or any of its mechanism. Usually, it is designed to house, fix, protect, guide, and/or engage with any of the inner components of the drug delivery device (e.g., the drive mechanism, cartridge, plunger, piston rod) by limiting the exposure to contaminants, such as liquid, dust, dirt etc. In general, the housing may be unitary or a multipart component of tubular or non-tubular shape. Usually, the exterior housing serves to house a cartridge from which a number of doses of a medicinal product may by dispensed.

In a more specific embodiment of instant invention, the exterior housing is provided with a plurality of maximum dose stops adapted to be abutted by a radial stop provided on the dose dial sleeve. Preferably, at least one of the maximum dose stops comprises a radial stop located between a helical thread and spline means provided at a second end of the housing. Alternatively; at least one of the maximum dose stops comprises a part of a raised window portion provided at a second end of the housing.

The term "engaged" according to instant invention shall particularly mean the interlocking of two or more components of the drive mechanism/drug delivery device, e.g. a spline, thread; or meshed teeth connection, preferably the interlocking of helical threads of components ("threadedly engaged").

The term "helical thread" according to instant invention shall preferably mean a full or part thread, e.g., a cylindrical spiral rib/groove, located on the internal and/or external surface of a component of the drug delivery device, having an essentially triangular or square or rounded section designed to allow continuous free rotational and/or axial movement between components. Optionally, a thread may be further designed to prevent rotational or axial movement of certain components in one direction.

The term "dose dial sleeve" according to instant invention shall mean an essentially tubular component of essentially circular cross-section having either:
 a) both an internal and external thread, or
 b) an internal thread, or
 c) an external thread.
Preferably, the dose dial sleeve according to instant invention comprises a helical thread having a lead, which is similar to, (preferably the same as the lead of the helical thread of the drive sleeve. In yet another preferred embodiment the dose dial sleeve is designed to indicate a selected dose of a dispensable product. This may be achieved by use of markings, symbols, numerals, etc., e.g. printed on the external surface of the dose dial sleeve or an odometer, or the like.

In a more specific embodiment of instant invention, the dose dial sleeve is provided with a plurality of radially extending members adapted to abut a corresponding plurality of radial stops provided at a second end of the housing.

The term "lead" according to instant invention shall preferably mean the axial distance a nut would advance in one complete revolution; preferably "lead" shall mean the axial distance through which a component having a helical thread, i.e. dose dial sleeve, drive sleeve, piston rod, etc., of the drive mechanism travels during one rotation. Therefore lead is a function of the pitch of the thread of the relevant component.

The term "pitch" according to instant invention shall preferably mean the distance between consecutive contours on a helical thread, measured parallel to the axis of the helical thread.

The term "drive sleeve" according to instant invention shall mean any essentially tubular component of essentially circular cross-section and which is further releasibly connected to the dose dial sleeve. In a preferred embodiment the drive sleeve is further engaged with the piston rod.

In a more particular embodiment of instant invention, the drive sleeve is provided at a first end with first and second flanges with an intermediate helical thread between the first and second flanges, having a nut disposed between the first and second flanges and keyed to the housing by spline means. Optionally, a first radial stop may be provided on a second face of the nut and a second radial stop may be provided on a first face of the second flange.

The term "releasibly connected" according to instant invention shall preferably mean that two components of instant mechanism or device are reversibly joined to each other, which allows coupling and decoupling, e.g. by means of a clutch.

The term "piston rod" according to instant invention shall mean a component adapted to operate through/within the housing, designed to translate axial movement through/within the drug delivery device, preferably from the drive sleeve to the piston, for the purpose of discharging/dispensing an injectable product. Said piston rod may be flexible or not. It may be a simple rod, a lead-screw, a rack and pinion system, a worm gear system, or the like. The "piston rod" shall further mean a component having a circular or non-circular cross-section. It may be made of any suitable material known by a person skilled in the art.

In a preferred embodiment, the piston rod comprises at least one, more preferably two, external and/or internal helical threads. In another preferred embodiment of the piston rod according to instant invention, a first helical thread is located at a first end and a second helical thread is located at a second end of the said piston rod, whereby the said threads may have the same or, preferably, opposite dispositions. In another preferred embodiment the piston rod of instant invention comprises threads having the same leads at the first and the second end.

In yet another preferred embodiment of instant invention the lead of the first helical thread of the piston rod shall be greater than the lead of the second helical thread. More preferred, the ratio of the leads of the helical threads of the said first and the second helical threads is 1:1, 01 to 1:20, even more preferred 1:1, 1 to 1:10. Preferably, one of the said threads is designed to engage with the drive sleeve.

Alternatively, in another preferred embodiment of the piston rod of instant invention, the piston rod is designed to have attached, optionally by means of a journal bearing, a toothed gear, and wherein said toothed gear is designed to mesh with the threads of the drive sleeve and the teeth of a toothed rack, whereby said toothed rack is fixed to the housing.

The term "first end" according to instant invention shall mean the proximal end. The proximal end of the device or a component of the device shall mean the end, which is closest to the dispensing end of the device.

The term "second end" according to instant invention shall mean the distal end. The distal end of the device or a component of the device shall mean the end, which is furthest away from the dispensing end of the device.

The term "clutch means" according to instant invention shall mean any means, which releasibly connects the dose dial sleeve and the drive sleeve and which is designed to allow rotation of the dose dial sleeve and the drive sleeve with respect to the housing when the dose dial sleeve and the drive sleeve are coupled and, when both are de-coupled, allows rotation of the dose dial sleeve with respect to the housing, but does not allow rotation of the drive sleeve with respect to the housing and allows axial movement of the drive sleeve. Preferably, the clutch means releasibly connects the drive sleeve to the housing. Accordingly, the term clutch means is any clutch engaging for the purpose of reversibly locking two components in rotation, e.g., by use of axial forces to engage a set of face teeth (saw teeth, dog teeth, crown teeth) or any other suitable frictional faces.

In a more specific embodiment of instant invention, a second end of the clutch means is provided with a plurality of dog teeth adapted to engage with a second end of the dose dial sleeve.

In an alternative embodiment, the clutch means of instant invention is a locking spring, operable, e.g., by means of a dose dial button, between a first, relaxed position, in which the dose dial sleeve is locked with respect to rotation with the drive sleeve and a second, deformed position, in which the dose dial sleeve is locked with respect to rotation with the housing.

In still another embodiment of instant invention, the drive mechanism further comprises a clicker means, optionally disposed between the clutch means and spline means provided on the housing.

Optionally, the clicker means comprises a sleeve provided at a first end with a helically extending arm, a free end of the arm having a toothed member; and at a second end with a plurality of circumferentially directed saw teeth adapted to engage a corresponding plurality of circumferentially saw teeth provided on the clutch means. Alternatively, the clicker means comprises a sleeve provided at a first end with at least one helically extending arm and at least one spring member, a free end of the arm having a toothed member, and at a second end with a plurality of circumferentially directed saw teeth adapted to engage corresponding plurality of circumferentially directed saw teeth provided on the clutch means.

In still another embodiment of the drive mechanism of the invention, the drive mechanism is provided with a first stop means, preferably in the form of an external flange on the dose dial sleeve, adapted to engage limiting means associated with the housing, preferably in the form of an internal flange in the housing, to limit the maximum dose which can be dialed. In yet another embodiment of the drive mechanism of the invention, the drive mechanism is further provided with a second stop means, preferably in the form of an external flange on the drive sleeve, adapted to engage limiting means, preferably in the form of a limiting nut keyed to the housing and mounted for rotation on an external threaded section of the drive sleeve, to provide an end of life stop.

A second aspect of instant invention provides an assembly for use in a drug delivery device comprising the drive mechanism according to instant invention.

A third aspect of the present invention provides a drug delivery device comprising the drive mechanism or the assembly according to instant invention.

A fourth aspect of the present invention provides a method of assembling a drug delivery device comprising the step of providing a drive mechanism or an assembly according to instant invention.

A fifth aspect of instant invention is the use of a drug delivery device according to instant invention for dispensing a medicinal product preferably dispensing a pharmaceutical formulation (e.g. solution, suspension etc.) comprising an active compound selected from the group consisting of insulin, growth hormone, low molecular weight heparin, their analogues and their derivatives.

BRIEF DESCRIPTION OF THE FIGURES

Without any limitation, the instant invention will be explained in greater detail below in connection with a preferred embodiment and with reference to the drawings in which:

FIG. 18 shows a sectional side view of a third embodiment of the drug delivery device in accordance with the present invention in a first, cartridge full, position; FIG. 19 shows a sectional side view of the drug delivery device of FIG. 18 in a second, maximum first dose dialed, position;

FIG. 20 shows a sectional side view of the drug delivery device of FIG. 18 in a third, maximum first dose dispensed, position;

FIG. 21 shows a sectional side view of the drug delivery device of FIG. 18 in a fourth, final dose dialed, position;

FIG. 22 shows a sectional side view of the drug delivery device of FIG. 18 in a fifth final dose dispensed, position;

DETAILED DESCRIPTION

Example 1

Figure 1:
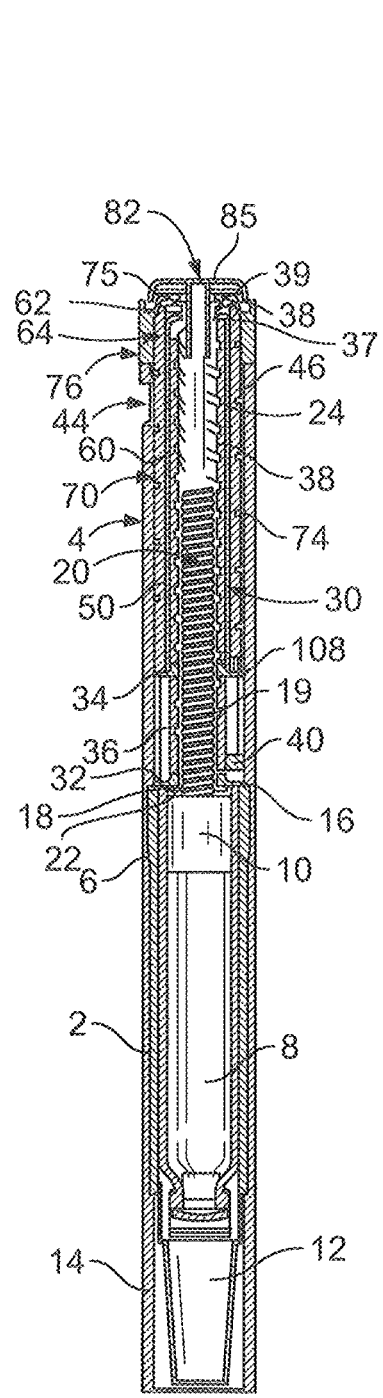
FIG. 1 shows a sectional view of a first embodiment of the drug delivery device in accordance with the present invention in a first, cartridge full, position.
Figure 2:
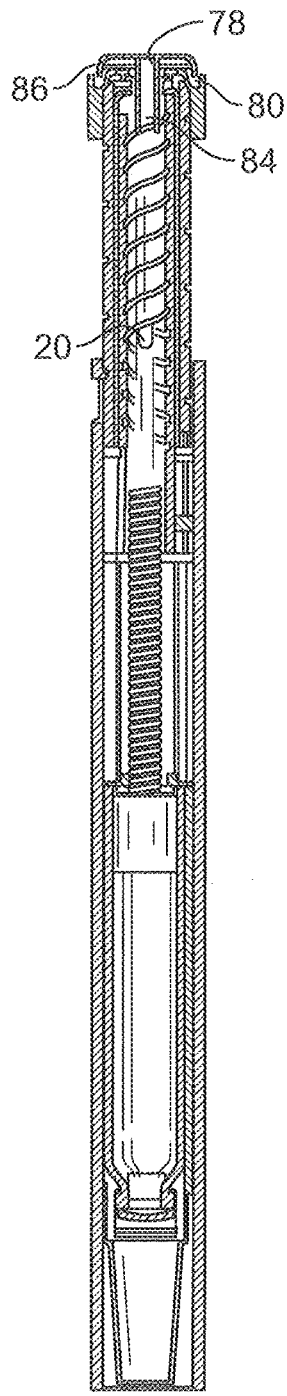
FIG. 2 shows a sectional view of the drug delivery device of FIG. 1 in a second, maximum first dose dialed, position.
Figure 3:
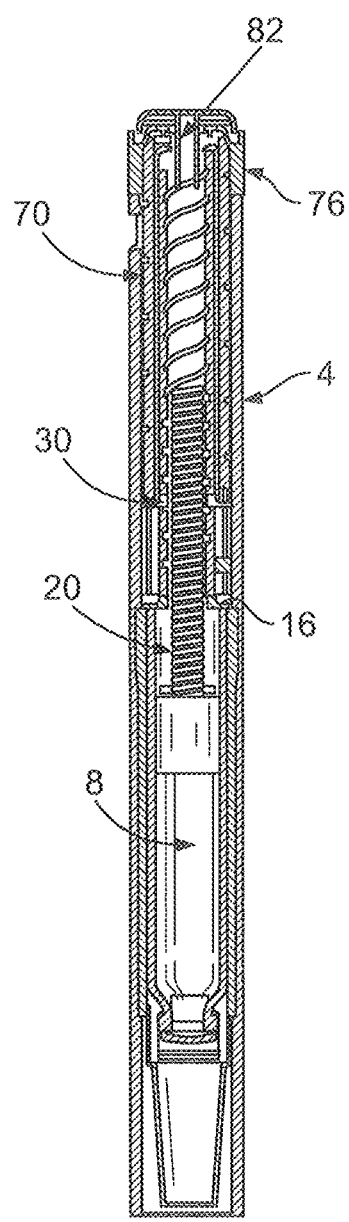
FIG. 3 shows a sectional view of the drug delivery device of FIG. 1 in a third, maximum first dose dispensed, position.
Figure 4:
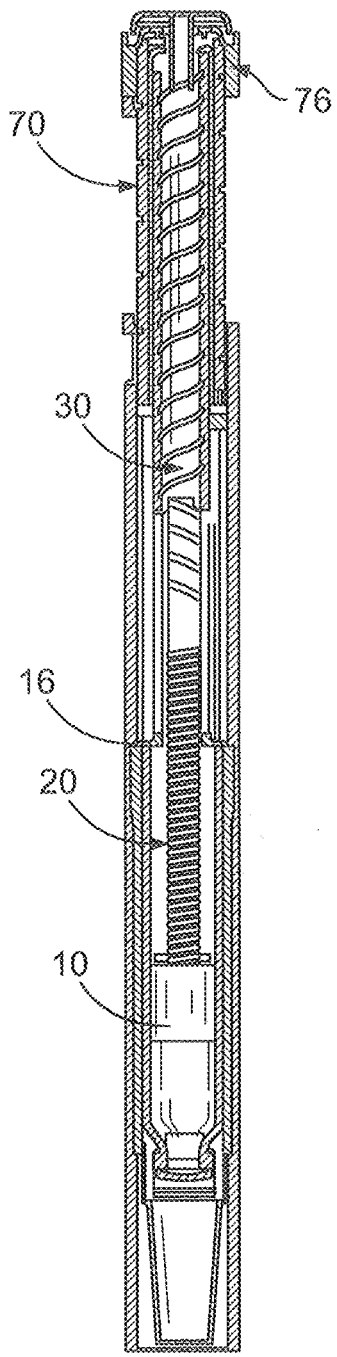
FIG. 4 shows a sectional view of the drug delivery device of FIG. 1 in a fourth, final dose dialed, position.
Figure 5:
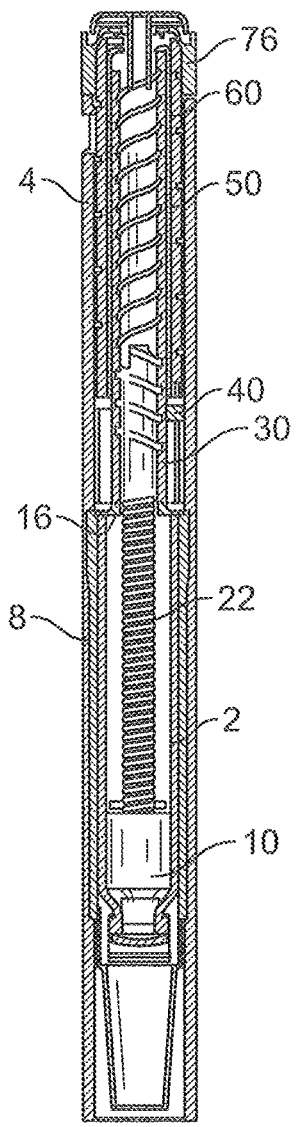
FIG. 5 shows a sectional view of the drug delivery device of FIG. 1 in a fifth, final dose dispensed, position.

Referring first to FIGS. 1 to 5, there is shown a drug delivery device in accordance with the present invention in a number of positions.

The drug delivery device comprises a housing having a first cartridge retaining part 2, and second main (exterior) housing part 4. A first end of the cartridge retaining means 2 and a second end of the main housing 4 are secured together by retaining features 6. In the illustrated embodiment, the cartridge retaining means 2 is secured within the second end of the main housing 4.

A cartridge 8 from which a number of doses of a medicinal product may be dispensed is provided in the cartridge retaining part 2. A piston 10 is retained in a first end of the cartridge 8.

A removable cap 12 is releasably retained over a second end of the cartridge retaining part 2. In use the removable cap 12 can be replaced by a user with a suitable needle unit (not shown). A replaceable cap 14 is used to cover the cartridge retaining part 2 extending from the main housing 4. Preferably, the outer dimensions of the replaceable cap 14 are similar or identical to the outer dimensions of the main housing 4 to provide the impression of a unitary whole when the replaceable cap 14 is in position covering the cartridge retaining part 2.

In the illustrated embodiment, an insert 16 is provided at a first end of the main housing 4. The insert 16 is secured against rotational or longitudinal motion. The insert 16 is provided with a threaded circular opening 18 extending therethrough. Alternatively, the insert may be formed integrally with the main housing 4 having the form of a radially inwardly directed flange having an internal thread.

A first thread 19 extends from a first end of a piston rod 20. The piston rod 20 is of generally circular section. The first end of the piston rod 20 extends through the threaded opening 18 in the insert 16. A pressure foot 22 is located at the first end of the piston rod 20. The pressure foot 22 is disposed to abut a second end of the cartridge piston 10. A second thread 24 extends from a second end of the piston rod 20. In the illustrated embodiment the second thread. 24 comprises a series of part threads rather than a complete thread. The illustrated embodiment is easier to manufacture and helps to reduce the overall force required for a user to actuate the device when dispensing the medicinal product.

The first thread 19 and the second thread 24 are oppositely disposed. The second end of the piston rod 20 is provided with a receiving recess 26.

A drive sleeve 30 extends about the piston rod 20. The drive sleeve 30 is generally cylindrical. The drive sleeve 30 is provided at a first end with a first radially extending flange 32. A second radially extending flange 34 is provided spaced distance along the drive sleeve 30 from the first flange 32. An intermediate thread 36 is provided on an outer part of the drive sleeve 30 extending between the first flange 32 and the second flange 34. A helical groove (thread) 38 extends along the internal surface of the drive sleeve 30. The second thread 24 of the piston rod 20 is adapted to work within the helical groove 38.

A first end of the first flange 32 is adapted to conform to a second side of the insert 16.

A nut 40 is located between the drive sleeve 30 and the main housing 2, disposed between the first flange 32 and the second flange 34. In the illustrated embodiment the nut 40 is a half-nut. This assists in the assembly of the device. The nut 40 has an internal thread matching the intermediate thread 36. The outer surface of the nut 40 and an internal surface of the main housing 4 are keyed together by splines 42 (FIGS. 10, 11, 15 and 16) to prevent relative rotation between the nut 40 and the main housing 4, while allowing relative longitudinal movement therebetween.

A shoulder 37 is formed between a second end of the drive sleeve 30 an extension 47 provided at the second end of the drive sleeve 30. The extension 47 has reduced inner and outer diameters in comparison to the remainder of the drive sleeve 30. A second end of the extension 47 is provided with a radially outwardly directed flange 39.

A clicker 50 and a clutch 60 are disposed about the drive sleeve 30 between the drive sleeve 30 and a dose dial sleeve 70 (described below).

Figure 6:
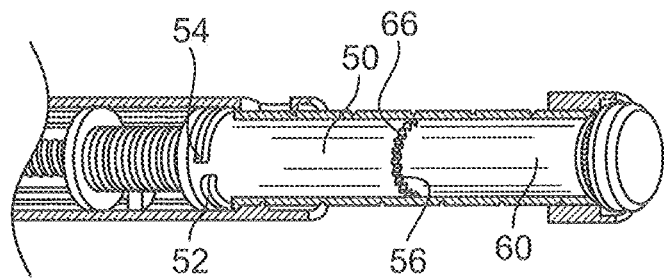
FIG. 6 shows a cut-away view of a first detail of the drug delivery device of FIG. 1.
Figure 7:
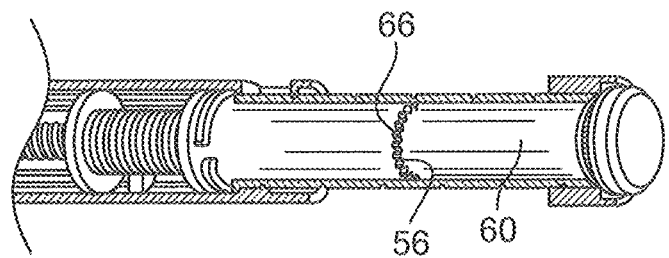
FIG. 7 shows a partially cut-away view of a second detail of the drug delivery device of FIG. 1.

The clicker 50 is located adjacent the second flange 34 of the drive sleeve 30. The clicker 50 is generally cylindrical and is provided at a first end with a flexible helically. extending arm 52 (FIG. 6). A free end of the arm 52 is provided with a radially directed toothed member 54. A second end of the clicker 50 is provided with a series of circumferentially directed saw teeth 56 (FIG. 7). Each saw tooth comprises a longitudinally directed surface arid an inclined surface.

In an alternative embodiment (not shown) the clicker further includes at least one spring member. The at least one spring member assists in the resetting of the clutch 60 following dispense.

Figure 8:
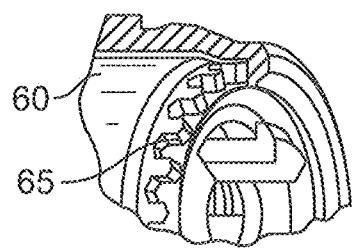
FIG. 8 shows a partially cut-away view of a third detail of the drug delivery device of FIG. 1.

The clutch 60 is located adjacent the second end of the drive sleeve 30. The clutch 60 is generally cylindrical and is provided at a first end with a series of circumferentially directed saw teeth 66 (FIG. 7). Each saw tooth comprises a longitudinally directed surface and an inclined surface. Towards the second end 64 of the clutch 60 there is located a radially inwardly directed flange 62. The flange 62 of the clutch 60 is disposed between the shoulder 37 of the drive sleeve 30 and the radially outwardly directed flange 39 of the extension 38. The second end of the clutch 60 is provided with a plurality of dog teeth 65 (FIG. 8). The clutch 60 is keyed to the drive sleeve 30 by way of splines (not shown) to prevent relative rotation between the clutch 60 and the drive sleeve 30.

In the illustrated embodiment, the clicker 50 and the clutch 60 each extend approximately half the length of the drive sleeve 30. However, it will be understood that other arrangements regarding the relative lengths of these parts are possible.

The clicker 50 and the clutch 60 are engaged as shown in FIG. 7.

A dose dial sleeve 70 is provided outside of the clicker 50 and clutch 60 and radially inward of the main housing 4. A helical groove 74 is provided about an outer surface of the dose dial sleeve 70.

Figure 15:
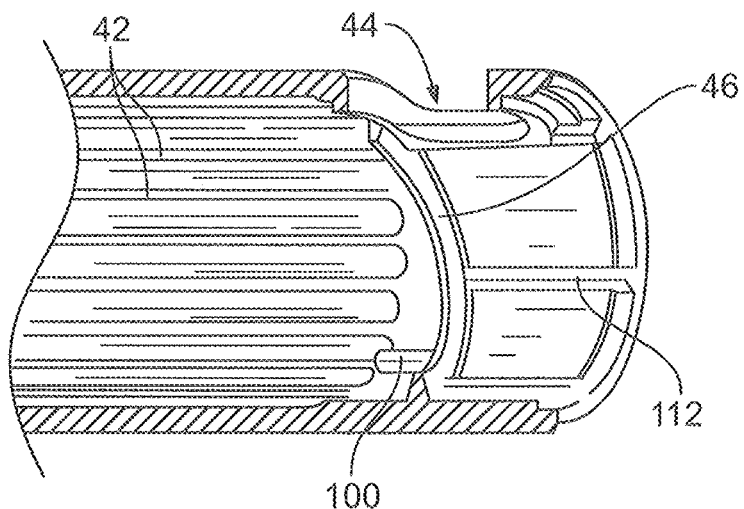
FIG. 15 shows a cut-away view of a first part of a main housing of the drug delivery device of FIG. 1.
Figure 16:
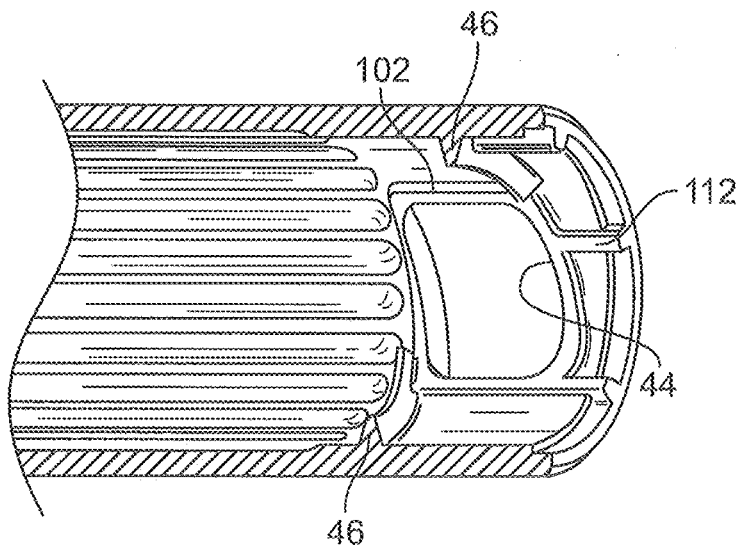
FIG. 16 shows a cut-away view of a second part of the main housing of the drug delivery device of FIG. 1.

The main housing 4 is provided with a window 44 through which a part of the outer surface of the dose dial sleeve may be seen. The main housing 4 is further provided with a helical rib (thread) 46, adapted to be seated in the helical groove (thread) 74 on the outer surface of the dose dial sleeve 70. The helical rib 46 extends for a single sweep of the inner surface of the main housing 4. A first stop 100 is provided between the splines 42 and the helical rib 46 (FIG. 15). A second stop 102, disposed at an angle of 180° to the first stop 100 is formed by a frame surrounding the window 44 in the main housing 4 (FIG. 16).

Conveniently, a visual indication of the dose that may be dialed, for example reference numerals (not shown), is provided on the outer surface of the dose dial sleeve 70. The window 44 conveniently only allows to be viewed a visual indication of the dose currently dialed.

A second end of the dose dial sleeve 70 is provided with an inwardly directed flange in the form of a number of radially extending members 75. A dose dial grip 76 is disposed about an outer surface of the second end of the dose dial sleeve 70. An outer diameter of the dose dial grip 76 preferably corresponds to the outer diameter of the main housing 4. The dose dial grip 76 is secured to the dose dial sleeve 70 to prevent relative movement therebetween. The dose dial grip 76 is provided with a central opening 78. An annular recess 80 located in the second end of the dose dial grip 76 extends around the opening 78.

A button 82 of generally "T" section is provided at a second end of the device. A stem 84 of the button 82 may extend through the opening 78 in the dose dial grip 76, through the inner diameter of the extension 47 of the drive sleeve 30 and into the receiving recess 26 of the piston rod 20. The stem 84 is retained for limited axial movement in the drive sleeve 30 and against rotation with respect thereto. A head 85 of the button 82 is generally circular. A skirt 86 depends from a periphery of the head 85. The skirt 86 is adapted to be seated in the annular recess 80 of the dose dial grip 76.

Figure 9:
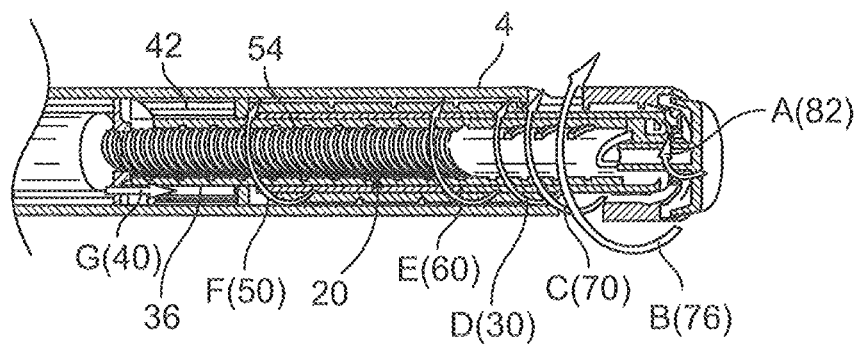
FIG. 9 shows the relative movement of parts of the drug delivery device shown in FIG. 1 during dialing up of a dose.
Figure 10:
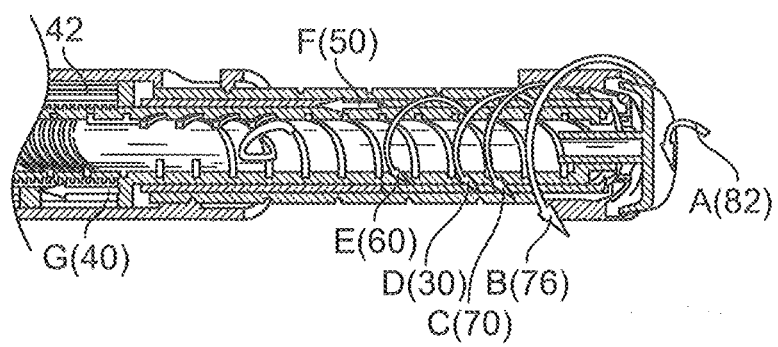
FIG. 10 shows the relative movement of parts of the drug delivery device shown in FIG. 1 during dialing down of a dose.
Figure 11:
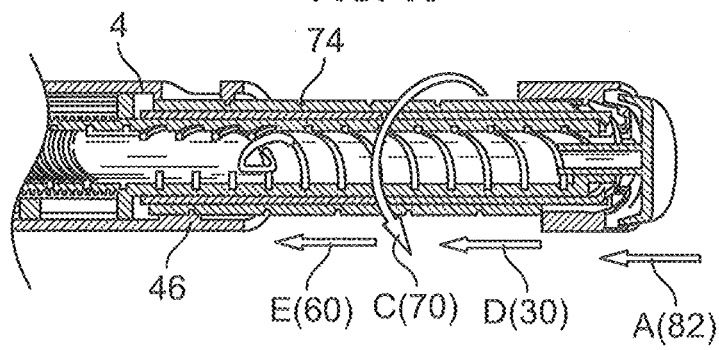
FIG. 11 shows the relative movement of parts of the drug delivery device shown in FIG. 1 during dispensing of a dose.

Operation of the drug delivery device in accordance with the present invention will now be described. In FIGS. 9, 10 and 11 arrows A, B, C, D, E, F and G represent the respective movements of the button 82, the dose dial grip 76, the dose dial sleeve 70, the drive sleeve 30, the clutch 60, the clicker 50 and the nut 40.

To dial a dose (FIG. 9) a user rotates the dose dial grip 76 (arrow B). With the clicker 50 and clutch 60 engaged, the drive sleeve 30, the clicker 50, the clutch 60 and the dose dial sleeve 70 rotate with the dose dial grip 76.

Audible and tactile feedback of the dose being dialed is provided by the clicker 50 and the clutch 60. Torque is transmitted through the saw teeth 56, 66 between the clicker 50 and the clutch 60. The flexible arm 52 deforms and drags the toothed member 54 over the splines 42 to produce a click. Preferably, the splines 42 are disposed such that each click corresponds to a conventional unit dose, or the like.

Figure 12:
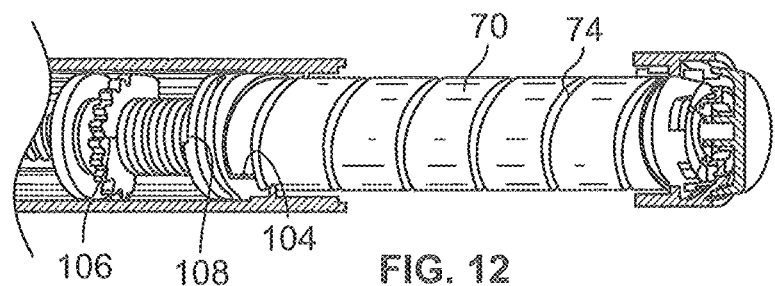
FIG. 12 shows a partially cut-away view of the drug delivery device of FIG. 1 in the second, maximum first dose dialed, position.

The helical groove 74 on the dose dial sleeve 70 and the helical groove 38 in the drive sleeve 30 have the same lead. This allows the dose dial sleeve 70 (arrow C) to extend from the main housing 4 and the drive sleeve 30 (arrow D) to climb the piston rod 20 at the same rate. At the limit of travel, a radial stop 104 (FIG. 12) on the dose dial sleeve 70 engages either the first stop 100 or the second stop 102 provided on the main housing 4 to prevent further movement. Rotation of the piston rod 20 is prevented due to the opposing directions of the overhauled and driven threads on the piston rod 20.

Figure 13:
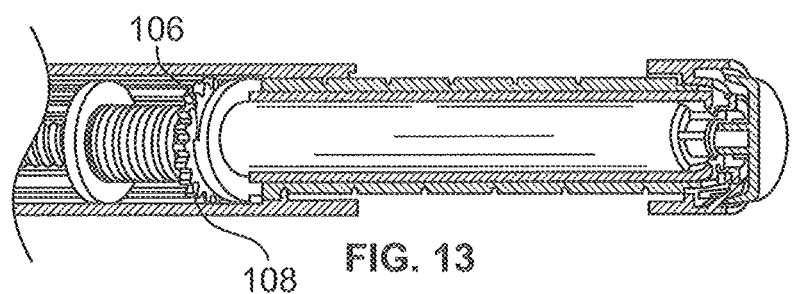
FIG. 13 shows a partially cut-away view of the drug delivery device of FIG. 1 in the fourth, final dose dialed, position.

The nut 40, keyed to the main housing 4, is advanced along the intermediate thread 36 by the rotation of the drive sleeve 30 (arrow D). When the final dose dispensed position (FIGS. 4, 5 and 13) is reached, a radial stop 106 formed on a second surface of the nut 40 abuts a radial stop 108 on a first surface of the second flange 34 of the drive sleeve 30, preventing both the nut 40 and the drive sleeve 30 from rotating further.

In an alternative embodiment (not shown) a first surface of the nut 40 is provided with a radial stop for abutment with a radial stop provided on a second surface of the first flange 32. This aids location of the nut 40 at the cartridge full position during assembly of the drug delivery device.

Should a user inadvertently dial beyond the desired dosage, the drug delivery device allows the dosage to be dialed down without dispense of medicinal product from the cartridge (FIG. 10). The dose dial grip 76 is counter rotated (arrow 13). This causes the system to act in reverse. The flexible arm 52 preventing the clicker 50 from rotating. The torque transmitted through the clutch 60 causes the saw teeth 56, 66 to ride over one another to create the clicks corresponding to dialed dose reduction. Preferably the saw teeth 56, 66 are so disposed that the circumferential extent of each saw tooth corresponds to a unit dose.

When the desired dose has been dialed, the user may then dispense this dose by depressing the button 82 (FIG. 11). This displaces the clutch 60 axially with respect to the dose dial sleeve 70 causing the dog teeth 65 to disengage. However the clutch•60 remains keyed in rotation to the drive sleeve 30. The dose dial sleeve 70 and associated dose dial grip 76 are now free to rotate (guided by the helical rib 46 located in helical groove 74).

The axial movement deforms the flexible arm 52 of the clicker 50 to ensure the saw teeth 56, 66 cannot be overhauled during dispense. This prevents the drive sleeve 30 from rotating with respect to the main housing 4 though it is still free to move axially with respect thereto. This deformation is subsequently used to urge the clicker 50, and the clutch 60, back along the drive sleeve 30 to restore the connection between the clutch 60 and the dose dial sleeve 70 when pressure is removed from the button 82

Figure 14:
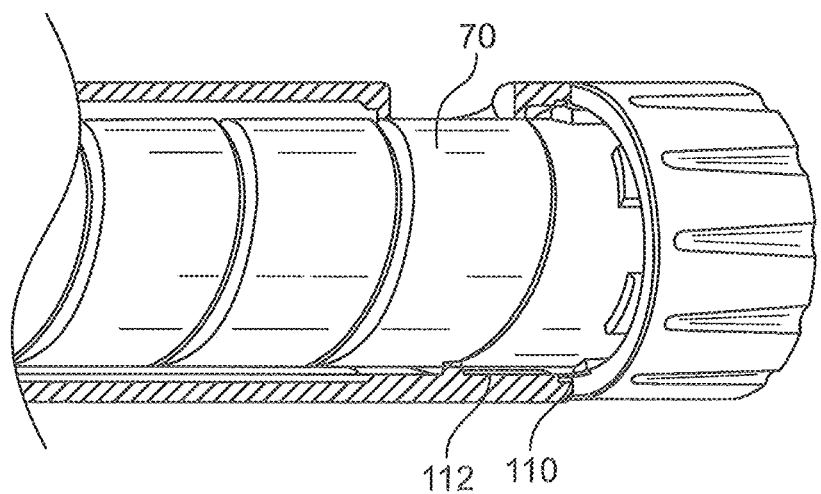
FIG. 14 shows a partially cut-away view of the drug delivery device of FIG. 1 in one of the first, third or fifth positions.

The longitudinal axial movement of the drive sleeve 30 causes the piston rod 20 to rotate though the opening 18 in the insert 16, thereby to advance the piston 10 in the cartridge 8. Once the dialed dose has been dispensed, the dose dial sleeve 70 is prevented from further rotation by contact of a plurality of members 110 (FIG. 14) extending from the dose dial grip 76 with a corresponding plurality of stops 112 formed in the main housing 4 (FIGS. 15 and 16). In the illustrated embodiment, the members 110 extend axially from the dose dial grip 76 and have an inclined end surface. The zero dose position is determined by the abutment of one of the axially extending edges of the members 110 with a corresponding stop 112.

Example 2

Figure 17:
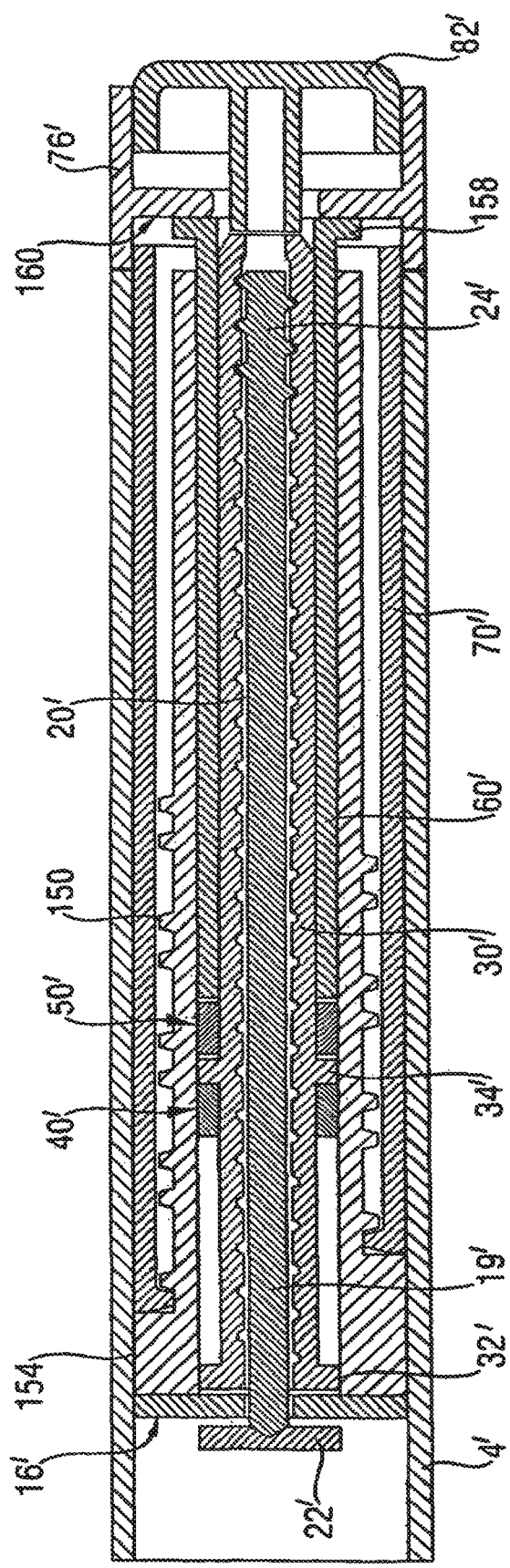
FIG. 17 shows a sectional view of a second embodiment of the drive mechanism according to instant invention in a first, cartridge full, position.
Figure 23:
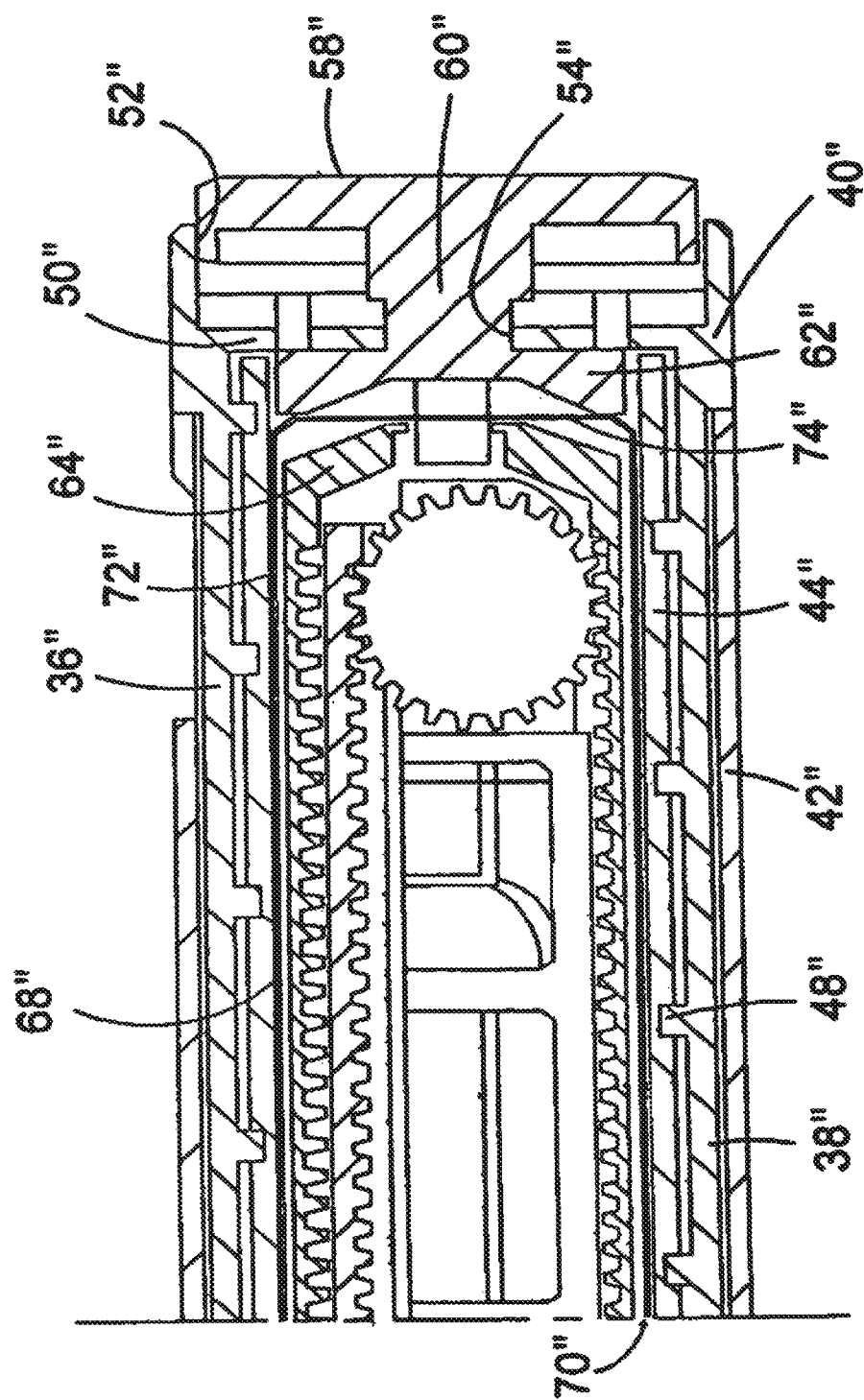
FIG. 23 shows a fragment of the drug delivery device of FIG. 18 in a larger scale.
Figure 24:
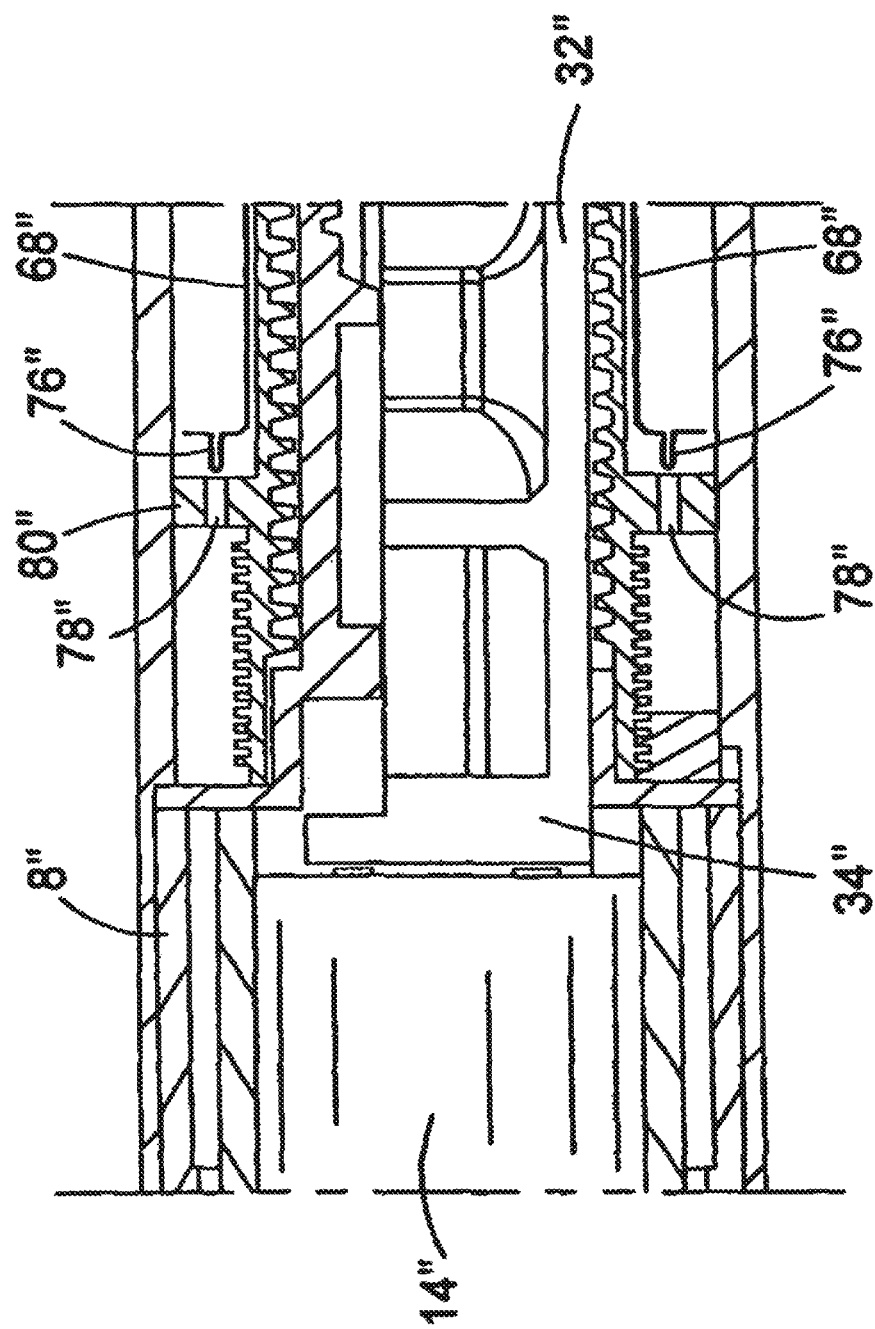
FIG. 24 shows a further fragment of the drug delivery device of FIG. 18 in a larger scale.

In another embodiment of the invention (FIG. 17) there is seen a drive mechanism comprising a second main housing 4' having a first end and a second end. A cartridge, containing medicinal product, can be mounted to the first end of the second main housing 4' and retained by any suitable means. The cartridge and its retaining means are not shown in the illustrated embodiment. The cartridge may contain a number of doses of a medicinal product and also typically contains a displaceable piston. Displacement of the piston causes the medicinal product to be expelled from the cartridge via a needle (also not shown).

In the illustrated embodiment, an insert 16' is provided within the main housing 4'. The insert 16' is secured against rotational and axial motion with respect to the second main housing 4'. The insert 16' is provided with a threaded circular opening extending therethrough. Alternatively, the insert may be formed integrally with the second main housing 4'.

An internal housing 154 is also provided within the second main housing 4'. The internal housing 154 is secured against rotational and axial motion with respect to the second main housing 4'. The internal housing 154 is provided with a circular opening extending through its length in which a series of longitudinally directed splines are formed. A helical thread 150 extends along the outer cylindrical surface of the internal housing 154. Alternatively, the internal housing may be formed integrally with the second main housing 4' and/or with the insert 16'.

A first thread 19' extends from a first end of a piston rod 20'. The piston rod 20' is of generally circular section. The first end of the piston rod 20' extends through the threaded opening in the insert 16' and the first thread 19' of the piston rod 20' is engaged with the thread of the insert 16'. A pressure foot 22' is located at the first end of the piston rod 20'. The pressure foot 22' is disposed to abut a cartridge piston (not shown). A second thread 24' extends from a second end of the piston rod 20'. The first thread 19' and the second thread 24' are oppositely disposed.

A drive sleeve 30' extends about the piston rod 20'. The drive sleeve 30' is generally cylindrical. The drive sleeve 30' is provided at a first end with a first radially extending flange 32'. A second radially extending flange 34' is provided, spaced a distance along the drive sleeve 30' from the first flange 32'. An external helical thread (not shown) is provided on the outer part of the drive sleeve 30' extending between the first flange 32' and the second flange 34'. An internal helical thread extends along the internal surface of the drive sleeve 30'. The second thread 24' of the piston rod 20' is engaged with the internal helical thread of the drive sleeve 30'.

A nut 40' is located between the drive sleeve 30' and the internal housing 154, disposed between the first flange 32' and the second flange 34' of the drive sleeve 30'. The nut 40' can be either a 'half-nut' or a 'full-nut'. The nut 40' has an internal thread that is engaged with the external helical thread of the drive sleeve 30'. The outer surface of the nut 40' and an internal surface of the internal housing 154 are keyed together by means of longitudinally directed splines to prevent relative rotation between the nut 40' and the internal housing 154, while allowing relative longitudinal movement therebetween.

A clicker 50' and a clutch 60' are disposed about the drive sleeve 30', between the drive sleeve 30' and the internal housing 154.

The clicker 50' is located adjacent the second flange 34' of the drive sleeve 30'. The clicker 50' includes at least one spring member (not shown). The clicker 50' also includes a set of teeth (not shown) having a triangular profile disposed towards the second end of the drive mechanism. When compressed, the at least one spring member of the clicker 50' applies an axial force between the flange 34' of the drive sleeve 30' and the clutch 60'. The outer surface of the clicker 50' and an internal surface of the internal housing 154 are keyed together by means of longitudinally directed splines to prevent relative rotation between the clicker 50' and the internal housing 154, while allowing relative longitudinal movement therebetween.

The clutch 60' is located adjacent the second end of the drive sleeve 30'. The clutch 60' is generally cylindrical and is provided at its' first end with a plurality of teeth of triangular profile disposed about the circumference (not shown), that act upon the teeth of the clicker 50'. Towards the second end of the clutch 60' there is located a shoulder 158. The shoulder 158 of the clutch 60' is disposed between the internal housing 154 and a radially inwardly directed flange of the dose dial grip 76' (described below). The shoulder 158 of the clutch 60' is provided with a plurality of dog teeth (not shown) extending in the direction of the second end of the drive mechanism. The clutch 60' is keyed to the drive sleeve 30' by way of splines (not shown) to prevent relative rotation between the clutch 60' and the drive sleeve 30'.

A dose dial sleeve 70' is provided outside of the internal housing 154 and radially inward from the second main housing 4'. A helical thread is provided on an inner surface of the dose dial sleeve 70'. The helical thread of the dose dial sleeve 70' is engaged with the helical thread 150 of the internal housing 154.

The second main housing 4' is provided with a window (not shown) through which part of the outer surface of the dose dial sleeve 70' may be viewed. Conveniently, a visual indication of the dose that may be dialed, for example reference numerals (not shown), is provided on the outer surface of the dose dial sleeve 70'. Conveniently, the window of the second main housing 4' allows only the dose that is currently dialed to be viewed.

A dose dial grip 76' is located towards the second end of the drive mechanism. The dose dial grip 76' is secured against rotational and axial motion within respect to the dose dial sleeve 70'. The dose dial grip 76' is provided with a radially inwardly directed flange 160. The radially inwardly directed flange 160 of the dose dial grip 76' is provided with a plurality of dog teeth (not shown) extending in the direction of the first end of the drive mechanism to abut the dog teeth of the clutch 60'. Coupling and decoupling of the dog teeth of the dose dial grip 76' with the dog teeth of the clutch 60' provides a releasable clutch between the dose dial grip 76' and the clutch 60'.

A button 82' of generally "T" shaped cross-section is provided at a second end of the drive mechanism. A cylindrical feature of the button 82' extends towards the first end of the drive mechanism, through an opening in the dose dial grip 76' and into a recess in the drive sleeve 30'. The cylindrical feature of the button 82' is retained for limited axial movement in the drive sleeve 30' and against rotation with respect thereto. The cylindrical feature of the button 82' has lugs extending radially (not shown) that abut the second surface of the shoulder 158 of the clutch 60'. The second end of the button 82' is generally circular arid has a cylindrical skirt about its' periphery that descends towards the first end of the drive mechanism. The skirt of the button 82' is located radially inward from the dose dial grip 76'.

Operation of the drive mechanism in accordance with the present invention will now be described.

To dial a dose, a user rotates the dose dial grip 76'. The spring member of the clicker 50' applies an axial force to the clutch 60' in the direction of the second end of the drive mechanism. The force exerted by the spring member of the clicker 50' couples the dog teeth of the clutch 60' to the dog teeth of the dose dial grip 76' fir rotation. As the dose dial grip 76' is rotated, the associated dose dial sleeve 70', the drive sleeve 30' and the clutch 60' all rotate in unison.

Audible and tactile feedback of the dose being dialed is provided by the clicker 50' and the clutch 60'. As the clutch 60' is rotated, torque is transmitted from the teeth at the first end of the clutch 60' and the teeth of the clicker 50'. The clicker 50' cannot rotate with respect to the internal housing 154, so the at least one spring member of the clicker 50' deforms allowing the teeth of the clutch 60' to jump over the teeth of the dicker 50' producing an audible and tactile 'click'. Preferably; the teeth of the clicker 50' and the teeth of the clutch 60' are disposed such that each 'click' corresponds to a conventional unit of the medicinal product, or the like.

The helical thread of the dose dial sleeve 70' and the internal helical thread of the drive sleeve 30' have the same lead. This allows the dose dial sleeve 70' to advance along the thread 150 of the internal housing 154 at the same rate as the drive sleeve 30' advances along the second thread 24' of the piston rod 20'. Rotation of the piston rod 20' is prevented due to the opposing direction of the first thread 19' and the second thread 24' of the piston rod. 20'. The first thread 19' of the piston rod 20' is engaged with the thread of the insert 16' and so the piston rod 20' does not move with respect to the second main housing 4' while a dose is dialed.

The nut 40', keyed to the internal housing 154, is advanced along the external thread of the drive sleeve 30' by the rotation of the drive sleeve 30'. When a user has dialed a quantity of medicinal product that is equivalent to the deliverable volume of the cartridge, the nut 40' reaches a position where it abuts the second flange 34' of the drive sleeve 30'. A radial stop formed on the second surface of the nut 40' contacts a radial stop on the first surface of the second flange 34' of the drive sleeve 30', preventing both the nut 40' and the drive sleeve 30' from being rotated further.

Should a user inadvertently dial a quantity greater than the desired dosage, the drive mechanism allows the dosage to be corrected without dispense of medicinal product from the cartridge. The dose dial grip 76' is counter-rotated. This causes the system to act in reverse. The torque transmitted through the clutch 60 causes the teeth at the first end of the clutch 60' to ride over the teeth of the clicker 50' to create the clicks corresponding to the dialed dose reduction.

When the desired dose has been dialed, the user may then dispense this dose by depressing the button 82' in the direction of the first end of the drive mechanism. The lugs of the button 82' apply pressure to the second surface of the shoulder 158 of the clutch 60', displacing the clutch 60' axially with respect to the dose dial grip 76'. This causes the dog teeth on the shoulder 158 of the clutch 60' to disengage from the dog teeth of the dose dial grip 76'. However, the clutch 60' remains keyed in rotation to the drive sleeve 30'. The dose dial grip 76' and associated dose dial sleeve 70' are now free to rotate (guided by the helical thread 150 of the internal housing 154).

The axial movement of the clutch 60' deforms the spring member of the clicker 50' and couples the teeth at the first end of the clutch 60' to the teeth of the clicker 50' preventing relative rotation therebetween. This prevents the drive sleeve 30' from rotating with respect to the internal housing 154, though it is still free to move axially with respect thereto.

Pressure applied to the button 82' thus causes the dose dial grip 76' and the associated dose dial sleeve 70' to rotate into the second main housing 4'. Under this pressure the clutch 60', the clicker 50' and the drive sleeve 30' are moved axially in the direction of the first end of the drive mechanism, but they do not rotate. The axial movement of the drive sleeve 30' causes the piston rod 20' to rotate though the threaded opening in the insert 16', thereby to advance the pressure foot 22'. This applies force to the piston, causing the medicinal product to be expelled from the cartridge. The selected dose is delivered when the dose dial grip 76' returns to a position where it abuts the second main housing 4'.

When pressure is removed from the button 82', the deformation of the spring member of the clicker 50' is used to urge the clutch 60' back along the drive sleeve 30' to re-couple the dog teeth on the shoulder 158 of the clutch 60' with the dog teeth on the dose dial grip 76'. The drive mechanism is thus reset in preparation to dial a subsequent dose.

Example 3

Referring to FIGS. 18 to 22 there may be seen a drug delivery device in accordance with the present invention. The drug delivery device comprises a two-part housing 2" within which are located a cartridge 4" containing a medicinal product, means for setting or selecting the dose of medicinal product to be expelled and means for expelling the selected dose of medicinal product. The housing 2" is generally cylindrical in shape and houses a rack 6" to be described in more detail below. The cartridge 4" is located within a first part 8" of the housing 2". The dose setting means and the means for expelling the selected dose of medicinal product are retained, that is held, within a second part 10" of the housing 2". The first part 8" of the housing 2" and the second part 10" of the housing 2" may be secured together by any suitable means The cartridge 4" may be secured in position in the first part 8" of the housing 2" by any suitable means. A needle unit may be secured to a first end of the cartridge 4". A temporary covering 12" is shown in this position in the Figures. The cartridge 4" further comprises a displaceable piston 14". Advancing the piston 10" towards the first end of the cartridge 4" causes the medicinal product to be expelled from the cartridge 4" through the needle unit. A cap 16" is provided to cover the needle unit when the drug delivery device is not in use. The cap 16" may be releasably secured to the housing 2" by any suitable means.

The dose setting means and the means for expelling the selected dose of medicinal product will now be described in more detail. The rack 6" is located within a drive sleeve 18" located within the housing 2" and is fixed both axially and rotationally with respect to the housing 2" by any suitable means. The drive sleeve 18" comprises an internally threaded portion 20", which extends along substantially the entire internal surface of the sleeve. An internal toothed gear 22" is located within the drive sleeve 18" and has helical teeth which match the pitch of the internal thread of the drive sleeve 18". The internal thread of the drive sleeve 18" is a multistart thread with a lead which is the same as the lead of the helical thread of the dose dial sleeve, which will be described later. The drive sleeve 18" terminates in an externally threaded section 24" which extends from an end of the sleeve as far as an external circumferential flange 26" which projects from the drive sleeve 18". A limiting nut 28" is mounted for rotation on the externally threaded section 24" of the sleeve 14". The limiting nut 28" is keyed to the housing 2" by means of a plurality of longitudinally extending splines 30" which extend along the internal surface of the first portion 8" of the housing 2". In the Illustrated embodiment, the limiting nut 28" is shown as a half-nut, but a full nut could be used.

A .piston rod 32" is provided extending along the length of the rack 6" and through a hole in the end of the rack 6". The piston rod 32" is generally elongate and. is provided with a pressure foot 34". In use the pressure foot 34" is disposed to abut the cartridge piston 14". The toothed gear 22" is mounted on the end of the piston rod 32" remote from the pressure foot 34" in a journal bearing (not shown).

A dose dial sleeve 36" of generally cylindrical form comprises a first section 38" of first diameter and a second section 40" of larger second diameter: The first section is located within the housing 2".

The second section 40" of the dose dial sleeve 36" is preferably of the same outer diameter as the housing 2". The second part 10" of the housing 2" comprises an .external sleeve portion 42" surrounding a coaxial internal sleeve portion 44". The external sleeve portion 42" is closed to the internal sleeve portion 44" at a circular internal flange portion 46". The first section 38" of the dose dial sleeve 36" is located within the second part 10" of the housing 2", between the external sleeve portion 42" and the internal sleeve portion 44". An inner surface of the first section 38" and the outer surface of the internal sleeve portion 44" are provided with interengaging features to provide a helical thread 48" between the internal sleeve portion 44" of the second part 10" of the•housing 2" and the dose dial sleeve 36". This helical thread 48" has the same lead as the internal thread of the drive sleeve 18", as noted above. Within the helical track, a helical rib provided on the inner surface of the dose dial sleeve 36" may run. This enables the dose dial sleeve 36" to rotate about and along the housing 2".

The second section 40" of the dose dial sleeve 36" is provided with an end wall 50" adjacent its free end, which defines a central receiving area 52" between the end wall 50" and the free end of the dose dial sleeve 36"'. A through hole 54" is provided in the end wall 50". A dose button 56" of generally "T" shaped configuration is provided, the head 58" of which is retained within the receiving area 52" and the stem 60" of which is sized to pass through the through hole 54". The stem 60" of the button 56" is provided with a plurality of fingers 62" that are deformable to pass through the through hole 54"' of the end wall 50" only in the direction away from the free end of the dose dial sleeve 36".

The drive sleeve 18" is closed at its end remote from the externally threaded section 24" by an apertured end wall 64" from which a plurality of engagement features 66" project external to the drive sleeve .18".

A substantially U-shaped locking spring 68" comprising first and second legs 70", 72" joined by a link portion 74" is provided for longitudinal mounting on the exterior of the drive sleeve 18". The link portion 74" is of a length which is substantially equal to the external diameter of the drive sleeve 18". Each of the legs 70", 72" of the locking spring 68" terminates in a latch portion 76", the function of which will be described later.

When the device is assembled, the locking spring 68" urges the dose button 56" axially away from the piston rod 32" and drive sleeve 18", towards the inside of the end wall 50" of the dose dial sleeve 36". In this position, the dose button 56" is locked with respect to rotation with the dose dial sleeve 36". The dose button 56" is also permanently locked with respect to rotation with the drive sleeve 18".

An outer surface of the first section of the dose dial sleeve 36" is provided with graphics 82". The graphics are typically a sequence of reference numerals. The housing 2" is provided with an aperture or window 84" through which a portion of the graphics, representing a dosage value selected by the user, may be viewed.

The graphics 82" may be applied to the dose dial sleeve 36" by any suitable means. The graphics 82" may be printed directly on the dose dial sleeve 36" or may be provided in the form of a printed label encircling the dose dial sleeve 36". Alternatively the graphics may take the form of a marked sleeve clipped to the dose dial sleeve 36". The graphics may be marked in any suitable manner, for example by laser marking.

The external circumferential flange 26" which projects from the drive sleeve 18" is provided with a pair of diametrically opposed through apertures 78" sized to receive the corresponding latch portions 76" of the locking spring 68". A clicker projection 80" from the outer edge of the flange 26" is associated with each through aperture 78".

In FIG. 18, the drug delivery device is provided with a filled cartridge 4". To operate the drug delivery device a user must first select a dose. To set a dose the dose dial sleeve 36" is rotated with respect to the housing 2" until the desired dose value is visible through the window 84". The drive sleeve 18" is linked to the dose dial sleeve 36" and spirals out at the same rate during dialing. During the dialing of a dose, the locking spring 68 is straight and urges the dose button 56" axially away from the piston rod 32" and drive sleeve 18", towards the inside of the end wall 50" of the dose dial sleeve 36", thereby providing a clutch mechanism. The drive sleeve 18" therefore rotates over the toothed gear 22" that is located inside it. The relative rotation between the drive sleeve. 18" and the housing 2" causes an audible confirmation of the dose being dialed by engagement of the two clicker projections 80"•with the splines 30" which extend along the internal surface of the first portion 8"•of the housing 2".

The limiting nut 28" climbs up the drive sleeve 18"•in proportion to the dose dialed. The position of the limiting nut 28", which only moves along the external thread of the drive sleeve 18" when there is relative rotation between the drive sleeve 18" and the housing 2", corresponds to the amount of medicinal product remaining in the cartridge 4".

Once a desired dose has been set (as shown for example in FIG. 19), to deliver the dose the user depresses the dose button 56"•to urge the button 56"•against the locking spring 68". As the dose button 56"•pushes down on the spring 68"•, the clutch between the dose button 56" and the dose dial sleeve 36" is disengaged. The axial force applied from the dose button 56"•onto the dose dial sleeve 36" causes the dose dial sleeve 36" to spin into the housing 2" on the helical thread between the dose dial sleeve 36" and the housing 2". The locking spring 68"•deforms and the legs of the spring move axially down the drive sleeve 18". The latch portions 76" of the locking spring 68" engage in the through apertures 78" on the external flange 26" which projects from the drive sleeve 18" and maintain engagement between the clicker projections 80"•of the flange 26" with the grooves between the splines 30", locking the drive sleeve to the housing 2" and preventing the drive sleeve 18" from rotation relative to the housing 2" during dispensing of the dose. The drive sleeve 18"•is thus prevented from spinning and moves axially in, causing the toothed gear 22" to rotate against the fixed rack 6". The toothed gear 22", together with the piston rod 32" on which it is mounted, move along the rack 6"•a distance corresponding to one half of the distance by which the drive sleeve 18" moves axially, creating a 2:1 mechanical advantage. This has the two-fold benefit of allowing the display on the dose dial sleeve 36" to be larger for a given amount of travel of the piston 14" within the cartridge 4", that is for a given amount of medicament to be dispensed and secondly of halving the force required to dispense the dose.

The piston rod 32" is driven through the drive sleeve 18" towards the first end of the drug delivery device, thereby to advance the cartridge piston 14" and expel the desired dose of medicinal product. The piston rod 32" continues to advance until the drive sleeve 18" and dose dial sleeve 36" have returned to their initial positions (FIG. 20).

It can be seen that the dose selecting means and the dose expelling means extend beyond a second end of the housing 2" as the dose is selected and are returned within the housing 2" as the selected dose is expelled, Further dosages may be delivered as required. FIG. 21 shows an example of a subsequently selected dosage. As noted above, the position of the limiting nut 28" along the external thread of the drive sleeve 18" corresponds to the amount of medicinal product remaining in the cartridge 4"; such that when the nut 28" reaches the external flange 26" and can rotate no further this corresponds to no medicinal product remaining in the cartridge 4". It will be seen that if a user seeks to select a quantity of medical product greater than that remaining in the cartridge 4", this cannot be done since when the nut 28" stops rotating against the drive sleeve 18", the drive sleeve 18" and the housing 2" will become locked together preventing rotation of the drive sleeve 18" and hence the dose dial sleeve 36". This prevents the setting of a larger dose than the amount of medical product remaining within the cartridge 4". FIG. 22 shows a drug delivery device according to the present invention in which the entire medicinal product within the cartridge 4" has been expelled.

The illustrated embodiment of the device according to the invention further comprises a maximum dosage dial end stop. When the dose dial sleeve 36" is dialed fully out, the external flange 26" on the drive sleeve 18" engages the internal flange 46" in the housing•2". It will be seen that if the user tries to dial beyond the maximum dosage, this cannot be done. When the drive sleeve 18" stops rotating against the housing 2", the dose dial sleeve is also prevented from rotating. The reaction between the external flange 44" and the internal flange 86" indicates to the user that the maximum dose has been dialed.

The invention claimed is:

1. A drive mechanism for use in a drug delivery device comprising:
   a housing comprising an inner surface having longitudinal splines;
   a dose dial sleeve threadedly engaged with the housing;
   a drive sleeve having an outer surface and releasably connected to the dose dial sleeve, where a proximal end of the drive sleeve comprises a distal and a proximal radially extending flange where threads are disposed on the outer surface between the flanges; and
   an end of life nut threadedly engaged with the threads on the outer surface of the drive sleeve between the two radially extending flanges, where the end of life nut has an outer surface configured to engage the splines on the inner surface of the housing to prevent rotation of the end of life nut relative to the housing and the drive sleeve, and where the end of life nut translates distally relative to the drive sleeve during dose setting and is axially fixed relative to the drive sleeve during dose delivery.

2. The drive mechanism of claim 1 further characterized in that the end of life nut engages the distal radially extending flange when the end of life nut has reached a final dose dispensed position.

3. The drive mechanism of claim 1 where the end of life nut has a threaded inner surface of a same pitch as the threads on the outer surface of the drive sleeve.

4. The drive mechanism of claim 1 where the end of life nut is a half nut configured to allow attachment to the outer surface of the drive sleeve between the two radially extending flanges during assembly of the drug delivery device.

5. The drive mechanism of claim 4 where the threads on the outer surface of the drive sleeve between the two radially extending flanges is a part thread.

6. The drive mechanism of claim 5 where the half nut is configured to advance distally along the part thread when the drive sleeve is rotated during dose setting.

7. The drive mechanism of claim 6 further characterized in that the advance of the half nut is proportional to a dialed dose.

8. The drive mechanism of claim 5 where the half nut is configured to advance proximally along the part thread when the drive sleeve is rotated to reduce an inadvertently set dose.

9. The drive mechanism of claim 1 where a distal face of the proximal radially extending flange has a radial stop configured to engage a radial stop on a proximal face of the end of life nut when the end of life nut is in a cartridge full position.

* * * * *